(12) United States Patent
Houtz et al.

(10) Patent No.: US 7,745,693 B2
(45) Date of Patent: Jun. 29, 2010

(54) INHIBITORS OF PLANT PEPTIDE DEFORMYLASE FOR USE AS BROAD-SPECTRUM HERBICIDES AND METHODS FOR IDENTIFYING THE SAME

(75) Inventors: Robert L. Houtz, Lexington, KY (US); Lynnette M. A. Dirk, Lexington, KY (US); Mark Alan Williams, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/880,955

(22) Filed: Jul. 24, 2007

(65) Prior Publication Data

US 2008/0064599 A1 Mar. 13, 2008

(51) Int. Cl.
*C12N 15/87* (2006.01)
*C12N 9/00* (2006.01)
*C12N 9/78* (2006.01)
*C12N 15/70* (2006.01)
*C12Q 1/68* (2006.01)
*C12P 21/06* (2006.01)
*C07H 21/04* (2006.01)

(52) U.S. Cl. .................. 800/278; 435/183; 435/227; 435/252.3; 435/320.1; 435/6; 435/69.1; 536/23.2

(58) Field of Classification Search ............ 800/278; 504/116.1; 435/183, 227, 228, 23, 468
See application file for complete search history.

(56) References Cited

U.S. PATENT DOCUMENTS

| | | | |
|---|---|---|---|
| 5,985,273 A | 11/1999 | Reed et al. | |
| 6,211,438 B1 * | 4/2001 | Anderson et al. | 800/300 |
| 6,730,634 B1 * | 5/2004 | Houtz et al. | 504/116.1 |

FOREIGN PATENT DOCUMENTS

| | | |
|---|---|---|
| EP | 0911409 | 4/1999 |
| EP | 1033405 | 9/2000 |

OTHER PUBLICATIONS

Hou et al. Plant peptide deformylase: a novel selectable marker and herbicide target based on essential cotranslational chloroplast protein processing, Plant Biotechnol J. Mar. 2007;5(2):275-81.*
Branden et al. Introduction to protein structure, Gerald Publishing Inc., New York, p. 247, 1991.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Seffernick et al. Melamine deaminase and atrazine chlorohydrolase: 98 percent identical but functionally different, J Bacteriol. Apr. 2001;183(8):2405-10.*
Lynnette et al. Eukaryotic peptide deformylases. Nuclear-encoded and chloroplast-targeted enzymes in arabidopsis, Plant physiology, 2001, vol. 127, No. 1, pp. 97-107.*
Margolis et al. Resistance of *Streptococcus pneumoniae* to deformylase inhibitors is due to mutations in defB. Antimicrob Agents Chemother. Sep. 2001;45(9):2432-5.*
Dirk et al. 2001, Plant Physiol. 127(1):97-107.*
Duggleby et al. (Plant Physiol Biochem. Mar. 2008; 46(3):309-24. Epub Jan. 14, 2008. Review).*
Akers, Alan, "Molecular Biology as Virtual Biology: Limitations of Molecular Biology in Pesticide Discovery", 1996, pp. 85-91, vol. 46, Pesticide Science, Great Britain.
Chen et al., "Actinonin, a Naturally Occurring Antibacterial Agent, Is a Potent Deformylase Inhibitor", Biochemistry 2000, pp. 1256-1262, American Cancer Society, Washington, D.C.
Giglione et al., :Petide deformylase as a target for new generation, broad spectrum antimicrobial agents, MicroReview, Molecular Microbiology , 2000, 36(6): 1997-1205, Blackwell Science, Ltd., Oxford, England.
Giglione et al., "Identification of eukaryotic peptide deformylases reveals universality of N-terminal protein processing mechanisms", The EMBO Journal, Sep. 13, 2000, pp. 5916-5929, vol. 19, No. 21, European Molecular Biology Organization, France.
Meinnel, T., "Peptide Deformylase of Eukaryotic Protists: A Target for New Antiparasitic Agents", Parasitology Today, 2000, pp. 165-168, vol. 16, No. 4, Elsevier Science, Ltd. Oxford, England.
Braun et al., purification and sequencing of cytochrome b from potato reveals methionine cleavage of mitochondrially encoded protein, FEBS Letters 316: 128-132, 1993.

* cited by examiner

*Primary Examiner*—Richard Hutson
*Assistant Examiner*—Iqbal H Chowdhury
(74) *Attorney, Agent, or Firm*—Crowell & Moring, LLP

(57) ABSTRACT

The invention relates to a method of identifying herbicides and to the use of inhibitors of plant peptide deformylase as broad spectrum herbicides.

6 Claims, 7 Drawing Sheets

CLUSTAL W (1.8) multiple sequence alignment

```
E coli (ACCESSION AE000407 U00096)        ---------------------------------MSVLQVLHIPDERLR------  15
Arabidopsis (ACCESSION AC007591)          METLFRVSLRLLPVSAAVTCRSIRFPVSRPGSSHLLNRKLYNLPTSSSSS  50
                                                                           .*   *:  :*:    *

E coli (ACCESSION AE000407 U00096)        ----------------------------------KVAKPVEEVNAEIQR  30
Arabidopsis (ACCESSION AC007591)          LSTKAGWLLGLGEKKKKVDLPEIVASGDPVLHEKAREVDPGEIGSERIQK  100
                                                                            *   ..*  .   .**:

E coli (ACCESSION AE000407 U00096)        IVDDMFETMYAEEGIGLAATQVDIHQRIIVIDVSENRD----------  68
Arabidopsis (ACCESSION AC007591)          IIDDMIKVMRLAPGVGLAAPQIGVPLRIIVLEDTKEYISYAPKEILAQE 150
                                          *:***::.*    ****. *:: ****::   :::

E coli (ACCESSION AE000407 U00096)        ----ERLVLINPELLEKSGE-TGIEEGCLSIPEQRALVPRAEKVKIRALD 113
Arabidopsis (ACCESSION AC007591)          RRHFDLMVMVNPVLKERSNKKALFFEGCLSVDGFRAAVERYLEVVTGYD 200
                                              :.:*  :**::*:..  .  :   ****:      **:  *  *

E coli (ACCESSION AE000407 U00096)        RDGKPFELEADGLLAICIQHEMDHLVGKLFMDYLSPLKQQRIRQKVEKLD 163
Arabidopsis (ACCESSION AC007591)          RQGKRIEVNASGWQARILQHECDHLDGNLYVDKMVPRTFRTVDNLDLPLA 250
                                          * ** :*:  :*.* :* *** *** * ::::*: *::.: :::. :

E coli (ACCESSION AE000407 U00096)        RLKARA---   169
Arabidopsis (ACCESSION AC007591)          EGCPKLGPQ   259
                                                 . :
```

FIG. 1A-1

REFERENCE
Thompson J.D., Higgins D.G., Gibson T.J.;
"CLUSTAL W: improving the sensitivity of progressive multiple sequence alignment through sequence weighting, position-specific gap penalties and weight matrix choice."; Nucleic Acids Res. 22:4673-4680(1994).

ClustalW WWW Service at the European Bioinformatics Institute
www2.ebi.ac.uk/clustalw
Rodrigo Lopez, Services Programme Andrew Lloyd
The ClustalWWW server at the EBI
embnet.news volume 4.2 1997
www2.ebi.ac.uk/embnet.news/vol4_3/clustalW.html

FIG. 1A-2

```
AtDEF(AC007591.2)        LSTKAGWLLGLGEKKKKVDLPEIVASGDPVLHEKAREVDPGEIGSERIQKIIDDMIKVMR   60
Chlamydia(AE001687.1)    --------------MIRRLEYYGSPILRKKS---SPIAEITDEIRNLVSDMCDTME     39
                                       *   :   *.*:*::*:     .*   ..**

AtDEF(AC007591.2)        LAPGVGLAAPQIGVPLRIIVLEDTKEYISYAPKEEILAQERRHFDLMVMNPVLKERSNK  120
Chlamydia(AE001687.1)    AHRGVGLAAPQVGKNVSLFVMCVDRETE----DGELIFSESPR----VFINPVLSDPSET  91
                          :.********::*  : ::**:  ::..*    *  ::* *      **** .  *

AtDEF(AC007591.2)        KALFFEGCLSVDGFRAAVERYLEVVVTGYDRQGKRIEVNASGWQARILQHECDHLDGNLY  180
Chlamydia(AE001687.1)    PIIGKEGCLSIPGLRGEVFRPQKITVTAMDLNGKIFTEHLEGFTARIIMHETDHLNGVLY  151
                          :  *****: * *  *. *  :::**  * :***: :: .*: ***:  :**** *:**

AtDEF(AC007591.2)        VDKMVP--RTFRTVDNLDLPLAEGCPKLGPQ----                         209
Chlamydia(AE001687.1)    IDLMEEPKDPKKFKASLEKIKRRYNTHLSKEELVS                         186
                         :* *      .*:.:  :  *    .:*.
```

FIG. 1B

INHIBITORS OF PLANT PEPTIDE DEFORMYLASE FOR USE AS BROAD-SPECTRUM HERBICIDES AND METHODS FOR IDENTIFYING THE SAME

CROSS-REFERENCE TO RELATED APPLICATIONS

This application claims priority from U.S. patent application Ser. No. 10/680,100, filed Oct. 8, 2003, which is a divisional application of U.S. patent application Ser. No. 09/617,805, filed Jul. 14, 2000, now U.S. Pat. No. 6,730,634. Each of these prior applications is hereby incorporated by reference in its entirety.

FIELD OF THE INVENTION

The invention relates to a method of identifying herbicides and to the use of inhibitors of plant peptide deformylase as broad spectrum herbicides.

BACKGROUND

Ribosome-mediated synthesis of proteins begins with a methionine residue. In prokaryotes and eukaryotic organelles (mitochondria and chloroplasts), the methionyl moiety carried by the initiator tRNA is N-formylated prior to its incorporation into a polypeptide (Meinnel and Blanquet, J. Bacteriol. 175:7737-7740 (1993)). N-formylmethionine is therefore always incorporated at the N-terminus of a nascent polypeptide in prokaryotes (Adams, J. M. and Capecchi, M., Proc. Natl. Aca. Sci. U.S.A. 55:147-155 (1966); Webster et al., Proc. Natl. Acad. Sci. U.S.A. 55:155-161 (1966)). However, most mature proteins do not retain the N-formyl group (Marcker, K. and Sanger, F. J. Mol. Biol. 8:835-840 (1964)). Instead, the N-formylmethionine group is removed post- or co-translationally in a process known as deformylation, which is catalyzed by peptide deformylase.

Deformylation is catalyzed by peptide deformylase which cleaves the formyl group from the nascent polypeptide chain (Adams, J., J. Mol. Biol. 33:571-589 (1968); Livingston, D. M. and Leder, P., Biochemistry 8:435-443 (1969); Takeda, M. and Webster, R. E., Proc. Natl. Acad. Sci. U.S.A. 60:1487-1494 (1968)).

Prior to the present invention, research in the area of peptide deformylase activity and enzymology focused on the bacterial enzyme. For example, the structure of the core domain of *E. coli* peptide deformylase was solved by NMR (Meinnel, T. et al., J. Mol. Biol. 262:375-386 (1996)) and the structure of the full-length protein by X-ray crystallography (Chan et al., Biochemistry 36:13904-13909 (1997)). Becker et al., J. Biol. Chemistry 273(19): 11413-11416 (1998) solved the structure of the catalytically active *E. coli* enzyme in the nickel-bound form (PDF-Ni) and in inhibitor-complexed form.

More recently, Ragusa et al., J. Mol. Biol. 289: 1445-1457 (1999), investigated the substrate specificity of *Escherichia coli* peptide deformylase by measuring the efficiency of the enzyme to cleave formylpeptides. Durand et al., Archives Biochemistry and Biophysics, 367(2):297-302 (1999), tested a variety of peptide aldehydes and identified calpeptin as a potent inhibitor of *E. coli* and *B. subtilis* peptide deformylase.

The overall focus in the field has been engineering site-specific inhibitors of peptide deformylase with a goal of developing broad-spectrum antibiotics with low to no mammalian toxicity. Rajagopalan et al., Biochemistry 36:13910-13918 (1997), identified specific and potent inhibitors of the bacterial enzyme which are potentially novel and new antibiotic agents. Meinnel et al., Biochemistry 38:4287-4295 (1999) designed and synthesized substrate analogue inhibitors of bacterial peptide deformylase and studied their capacity to undergo hydrolysis. To aid in the design of both the cobalt and zinc containing *E. coli* peptide deformylase, Hao et al., Biochemistry 38:4712-4719 (1999), studied the structure of the protein-inhibitor complexes of the cobalt and zinc containing *E. coli* enzyme.

Prior to the present invention, it was generally accepted that peptide deformylase genes and proteins were absent from eukaryotic cells. The present invention unexpectedly establishes, for the first time, the existence of a peptide deformylase gene and protein in eukaryotic cells, particularly in plant cells. The inventors have found that the deformylase is a novel and suitable target for identifying new broad spectrum herbicides.

SUMMARY OF THE INVENTION

In a first aspect, the present invention relates to a plant peptide deformylase gene which is expressed in a higher plant. A particularly preferred higher plant is *Arabidopsis*. More particularly preferred is the strain *Arabidopsis thaliana*.

In additional aspects, the present invention relates to a nucleotide and amino acid sequence encoding a plant peptide deformylase.

In another aspect, the present invention relates to a recombinant vector comprising the peptide deformylase nucleotide sequence described above.

In another aspect, the invention relates to a host cell that is transformed or transfected with the recombinant vector of the invention. The host cell may be a prokaryotic cell, such as a bacterial cell, or a eukaryotic cell, such as a plant cell or a mammalian cell.

In yet another aspect, the present invention relates to an isolated or recombinantly expressed peptide deformylase polypeptide which is encoded by a plant peptide deformylase gene as described above.

In still another aspect, the present invention relates to a method for introducing the plant peptide deformylase gene into a cell which does not express said gene, which method comprises transforming a higher plant seed crop with the recombinant vector (vector containing a peptide deformylase gene) such that the cell expresses the peptide deformylase enzyme encoded by the gene. The cell may be a prokaryotic cell or a eukaryotic cell.

In another aspect, the present invention provides a method of identifying an inhibitor of plant peptide deformylase, said method comprising:

(a) incubating a catalytically effective amount of a plant peptide deformylase, with a suitable substrate, in the presence or absence of a candidate inhibitor compound, and (b) detecting and quantifying the enzyme product formed.

The method may further comprises comparing the amount of enzyme product formed in the presence and absence of said candidate inhibitor.

In a preferred embodiment, the method of the invention permits identification of inhibitors of peptide deformylase derived from *Arabidopsis thaliana*.

The invention also provides a method of identifying herbicides which comprises testing a compound in a peptide deformylase inhibition assay, and where a measurable reduction of plant peptide deformylase is observed, subjecting the compound to an in vivo test for herbicidal activity.

In another aspect, the invention relates to herbicides which act by inhibiting plant peptide deformylase and which are identified by the methods of the invention.

In another aspect, the invention provides a method of combating weeds comprising treating said weeds with a herbicide, wherein said herbicide is a compound which is an inhibitor of peptide deformylase. A preferred herbicide is actinonin, which is a potent inhibitor of plant peptide deformylase.

The invention also provides a method of controlling vegetation comprising applying to plant foliage a herbicidally effective amount of an inhibitor of peptide deformylase.

In a further aspect, the invention provides a method of inhibiting the activity of plant peptide deformylase comprising exposing said peptide deformylase to an effective amount of an inhibitor of said peptide deformylase.

Still further, the invention provides an antibody directed against peptide deformylase isolated from *Arabidopsis thaliana*. The antibody may be a polyclonal or a monoclonal antibody.

In an additional aspect, the invention also provides a transgenic plant, wherein said transgenic plant is engineered to be resistant to an inhibitor of plant peptide deformylase.

In a further aspect, the invention provides a herbicidal composition comprising an inhibitor of plant peptide deformylase. In accordance with the present invention, the inhibitor is a herbicide, i.e. a compound having herbicidal activity. The composition of the invention may also contain a herbicidally acceptable surfactant.

In yet another aspect, the present invention provides a method of controlling vegetation comprising applying to plant foliage a herbicidal composition, wherein said herbicidal composition comprises an inhibitor of plant peptide deformylase. Those of skill in the art would recognize that the herbicide actinonin may be included in compositions of the present invention.

Additional aspects of the invention will be described throughout the specification.

BRIEF DESCRIPTION OF THE FIGURES

FIG. 1A shows a CLUSTAL W (1.8) alignment of *Arabidopsis* (truncated to the ChloroP predicted transit peptide) SEQ ID NO: 8 and *E. coli* SEQ ID NO: 7 peptide deformylase proteins.

FIG. 1B shows a CLUSTAL W (1.8) alignment of *Arabidopsis* (truncated to the ChloroP predicted transit peptide) SEQ ID NO: 8 and *Chlamydia* peptide deformylase proteins SEQ ID NO: 10. All three conserved proteins motifs found in prokaryotic sequences are present in the *Arabidopsis* peptide deformylase (AtDEF1).

FIG. 4 shows detection of an expected size protein from ~100 µg *Arabidopsis* total protein extract (soluble, lane 2; insoluble, lane 3) by AtDEF1 antibody (Rabbit 95728) at.

1:50,000. Inclusion bodies (50 ng) used as antigen in making the antibody were included in the standard lane (lane 1).

Figure 5:

FIG. 5 shows ten-day old pea plants 48 hours after application of actinonin (2.5 mg/ml) in 0.1% Tween-20 (left) or treated with 0.1% Tween-20 alone (right).

Figure 6:
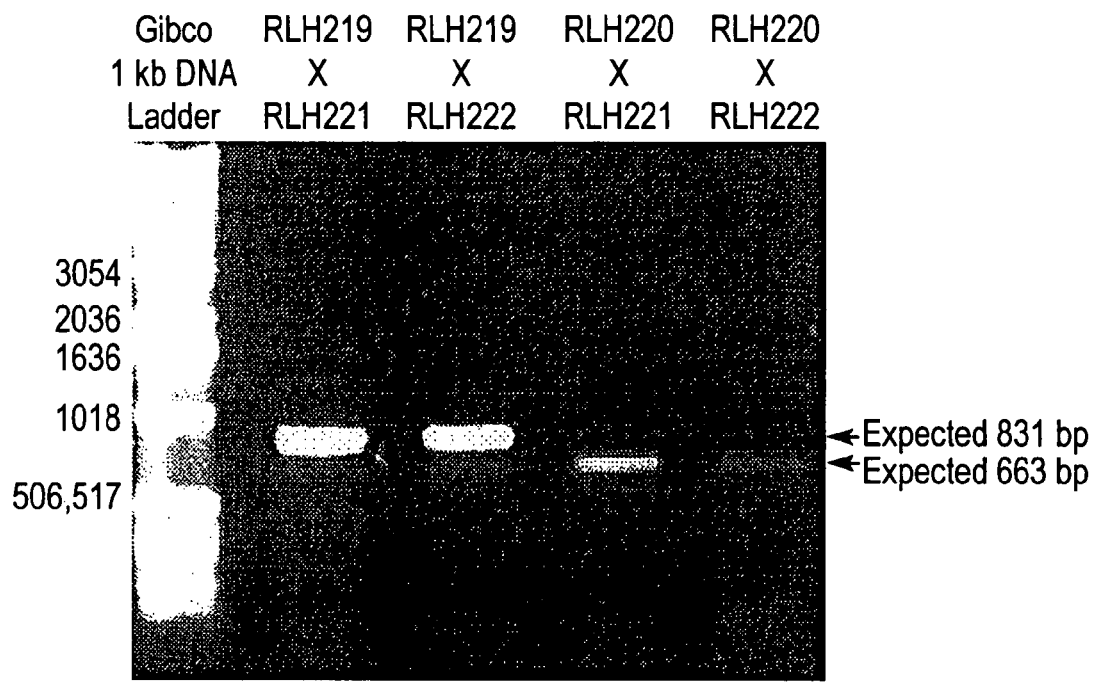

FIG. 6 is a 1% agarose gel in TBE buffer containing 0.1 µg/ml ethidium bromide and subjected to electrophoresis. Amplicons of Reverse Transcriptase-Polymerase Chain Reactions (RT-PCR) reactions of Atdef2 are depicted.

Figure 7:
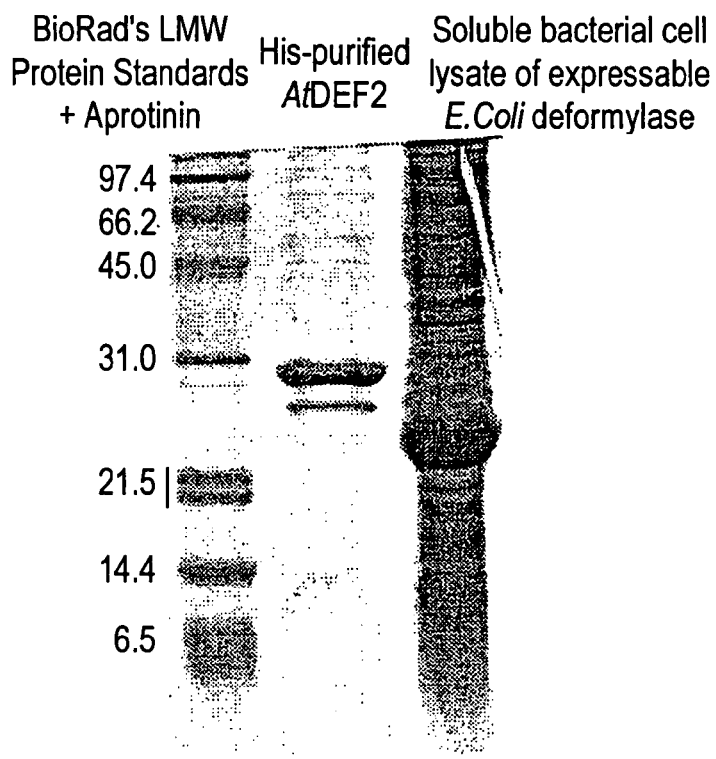

FIG. 7 is a 15% SDS-PAGE showing AtDEF2 after purification.

Figure 8:
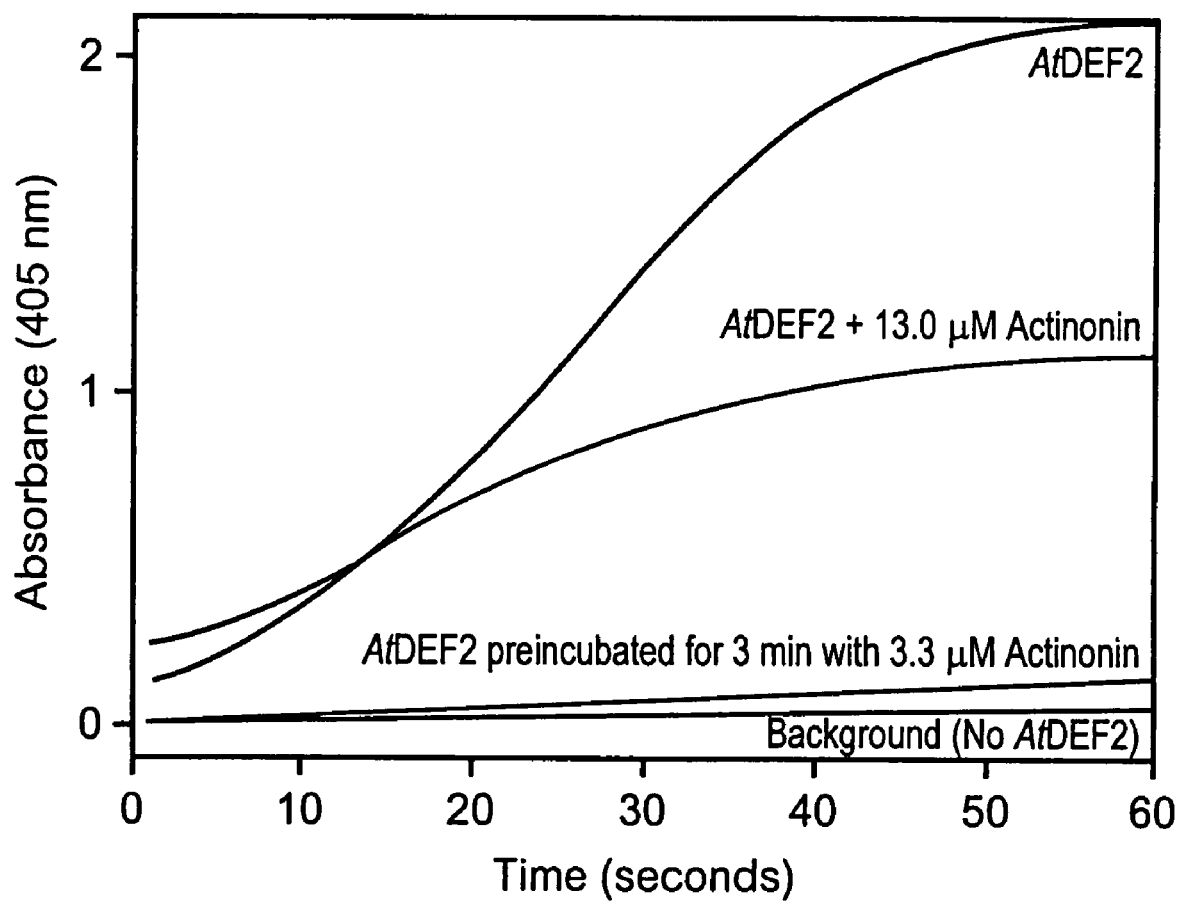

FIG. 8 shows spectrophotometric detection and quantitation of p-nitroaniline released from formyl-Met-Leu-p-nitroanilide substrate following sequential action of AtDEF2 and *Aeromonas proteolytica* aminopeptidase.

DETAILED DESCRIPTION OF THE INVENTION

As discussed above, the present inventors have found that plant cells contain a peptide deformylase gene and protein, and the deformylase provides a novel and suitable target for identifying new broad spectrum herbicides. The identification of this new target has widespread implications in the agricultural area. Methods of identifying inhibitors of this target will be useful for identifying new broad spectrum herbicides, which will be used to control the growth of weeds. Chemical weed control using herbicides is a powerful tool in the modern technological age. In fact, it has become almost a universal practice to use herbicides to control growth of undesirable vegetation such as weeds or plants.

A particularly useful type of herbicide is one having a broad spectrum of herbicidal activity. The use of broad spectrum herbicides offers the advantage of obviating the need for multiple herbicides. Since some weeds are resistant to herbicides, clearly there is a need for the identification of new targets of inhibition and for identification and production of effective herbicides that inhibit such targets.

The present invention is based, at least in part, on the discovery of a plant nuclear gene that encodes a chloroplast targeted peptide deformylase polypeptide. Utilizing sequence data obtained from the *Arabidopsis* genome sequencing project (Accession Number AC 007591), the present inventors have isolated a cDNA from *Arabidopsis thaliana* that encodes peptide deformylase. The gene has substantial homology to bacterial peptide deformylase. The deduced translation of this DNA sequence revealed the presence of all three conserved protein motifs associated with prokaryotic peptide deformylase. (See FIG. 1B for sequence alignment.)

Thus, the present invention provides a plant peptide deformylase gene which is expressed in higher plants. A particularly preferred higher plant is *Arabidopsis*. More particularly preferred is the strain *Arabidopsis thaliana*.

The invention also provides polynucleotide sequences which encode a plant peptide deformylase. In particular, the invention encompasses the polynucleotide sequences of Atdef1 and Atdef2 genes. Also within the scope of the invention are polynucleotide sequences encoding a plant peptide deformylase which have substantial identity to the polynucleotide sequence of Atdef1 or Atdef2. Such polynucleotide sequences are readily identifiable by those skilled in the art using techniques known in the art such as site-specific mutagenesis and hybridization technology, such as hybridization under stringent conditions.

The invention further provides an isolated and purified polynucleotide sequence which hybridizes under stringent conditions to the polynucleotide encoding the polypeptide comprising the amino acid sequence of AtDEF1 or AtDEF2 or a fragment thereof, as well as an isolated and purified polynucleotide which is complementary to the polynucleotide encoding the polypeptide comprising the amino acid sequence of AtDEF1 or AtDEF2 or a fragment thereof.

The invention also provides an isolated and purified polynucleotide sequence comprising the polynucleotide sequence of Atdef1 or a fragment thereof, and an isolated and purified polynucleotide variant having at least 70% polynucleotide sequence identity to the polynucleotide comprising the polynucleotide sequence of Atdef1 or Atdef2 or a fragment thereof. The invention also provides an isolated and purified polynucleotide having a sequence complementary to the polynucleotide comprising the polynucleotide sequence of Atdef1 or Atdef2 or a fragment thereof.

Amino acid sequences encoding a plant peptide deformylase are also within the purview of the present invention. Such amino acids sequences include but are not limited to the amino acid sequences of AtDEF1 and AtDEF2.

Additionally, and of equal importance, the inventors have identified a putative N-terminal targeting sequence for chloroplasts. (FIGS. 1a and 1b) Thus, perhaps as a remnant of its prokaryotic origins, the chloroplast has retained N-formylmethionine as its initiator of protein translation.

The present invention is based on a novel herbicidal mode of action, i.e., inhibition of plant peptide deformylase. Discovery of this novel mode of action opens up the opportunity for identifying novel chemicals that inhibit the enzyme target either directly or following metabolism to an active inhibitor in plants ("indirect inhibitors").

Because all non-parasitic plants contain chloroplasts, and deletion and/or mutation of peptide deformylase in prokaryotic organisms is lethal, it is expected that inhibition of peptide deformylase activity in the chloroplast will be lethal to plants.

Thus, the invention relates to the identification of compounds, as well as the development of new compounds capable of acting as highly specific inhibitors of chloroplastic peptide deformylase, for use as broad spectrum herbicides.

The invention provides a method of identifying potential herbicides which comprises testing a candidate in a peptide deformylase assay for direct and indirect inhibitors. Indirect inhibitors are those inhibitors that require conversion in plants.

More specifically, the invention relates to a method of identifying an inhibitor of plant peptide deformylase, said method comprising:

(a) incubating an effective amount of a plant peptide deformylase, with a suitable substrate, in the presence or absence of a candidate inhibitor compound; and (b) detecting and quantifying the enzyme product formed.

The method may further comprise comparing the amount of enzyme product formed in the presence and absence of said candidate inhibitor.

The invention permits identification of inhibitors of peptide deformylase derived from *Arabidopsis thaliana* as well as inhibitors of peptide deformylase derived from other plants including, but not limited to, soybean, sunflower, cotton, corn, tobacco, alfalfa, wheat, barley, oats, sorghum, hardwood and softwood trees, forage grasses, pea, canola, flax, tomato, sugar beet, potato, rice, lettuce and radish.

The invention employs an isolated or recombinantly expressed plant peptide deformylase polypeptide encoded by a plant peptide deformylase gene. The invention also encompasses variants of this polypeptide, and particularly those which retain peptide deformylase activity.

A cDNA for a peptide deformylase, such as an *Arabidopsis* peptide deformylase cDNA, may be engineered and inserted into bacterial expression vectors to verify functional activity, subcellular localization, and to generate a suitable amount of the protein for crystallization attempts and acquisition of antibodies.

Production of a recombinant plant peptide deformylase polypeptide may be achieved by a method comprising:

(a) transforming a suitable host cell with a vector comprising a gene encoding a plant peptide deformylase polypeptide, the gene being operably linked to suitable regulatory sequences;

(b) growing the transformed cell under conditions where the peptide deformylase is expressed.

To obtain a peptide deformylase polypeptide, recombinant host cells expressing the peptide deformylase polypeptide may be grown in a conventional manner in a suitable culture medium and then lysed using conventional means such as enzymatic degradation or detergents or the like. The expressed protein may be isolated as an insoluble inclusion body. Alternatively, the protein can be separated and purified by standard chromatography techniques.

Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion.

Suitable host cells are known to those of skill in the art and include, but are not limited to bacterial cells such as BL21 (DE3)pLysS, BL21(DE3), and GI724. Those of skill in the art would recognize that the host cell encompassed by the present invention may be a prokaryotic cell, such as a bacterial cell, or a eukaryotic cell, such as a plant cell or a mammalian cell.

Suitable expression vectors are known and routinely used in the art and may include, but are not limited to, pLEX and pET.

One type of recombinant vector, referred to herein as a recombinant molecule, comprises a nucleic acid molecule of the present invention operatively linked to an expression vector. The phrase operatively linked refers to insertion of a nucleic acid molecule into an expression vector in a manner such that the molecule is able to be expressed when transformed into a host cell. As used herein, an expression vector is a DNA or RNA vector that is capable of transforming a host cell and of effecting expression of a specified nucleic acid molecule. Preferably, the expression vector is also capable of replicating within the host cell. Expression vectors can be either prokaryotic or eukaryotic, and are typically viruses or plasmids. Expression vectors of the present invention include any vectors that function (i.e., direct gene expression) in recombinant cells of the present invention, including in bacterial, fungal, endoparasite, insect, other animal, and plant cells. Preferred expression vectors of the present invention can direct gene expression in bacterial, yeast, insect and mammalian cells and more preferably in the cell types disclosed herein.

In particular, expression vectors of the present invention contain regulatory sequences such as transcription control sequences, translation control sequences, origins of replication, and other regulatory sequences that are compatible with the recombinant cell and that control the expression of nucleic acid molecules of the present invention. In particular, recombinant molecules of the present invention include transcription control sequences. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in bacterial, yeast, insect and mammalian cells, such as, tac, lac, trp, trc, oxy-pro, omp/lpp, rrnB, bacteriophage lambda (such as lambda $P_L$ and lambda $P_R$ and fusions that include such promoters), bacteriophage T7, T7lac, bacteriophage T3, bacteriophage SP6, bacteriophage SP01, metallothionein, alpha-mating factor, *Pichia* alcohol oxidase, alphavirus subgenomic promoters (such as Sindbis virus subgenomic promoters), antibiotic resistance gene, baculovirus, *Heliothis zea* insect virus, vaccinia virus, herpesvirus, raccoon poxvirus, other poxvirus, adenovirus, cytomegalovirus (such as intermediate early promoters), simian virus 40, retrovirus, actin, retroviral long terminal repeat, Rous sarcoma virus, heat shock, phosphate and nitrate transcription control sequences as well as other sequences capable of controlling gene expression in prokaryotic or eukaryotic cells. Additional suitable transcription control sequences include tissue-specific promoters and enhancers as well as lymphokine-inducible promoters (e.g., promoters inducible by interferons or interleukins).

Purified peptide deformylase is highly active toward N-formylated peptide substrates, thus rendering these peptides suitable for use in the methods of the present invention. Suitable substrates include, but are not limited to formylated dipeptides and formyl-Met-Leu-p-nitroanilide as described by Wei and Pei, Analytical Biochemistry 250:29-34 (1997) and other formylated peptides as described by Rajagopalan et al., Biochemistry 36:13910-13918 (1997).

Peptide deformylase activity may be assessed by detecting and quantifying the amount of enzyme product formed in the method of the invention. Specifically, peptide deformylase activity can be quantified by measuring the amount of released p-nitroaniline (end product) from formyl-Met-Leu-p-nitroanilide using a coupled enzyme assay with *Aeronomonas proteolytica* aminopeptidase. This permits assessment of the catalytic properties of peptide deformylase using a series of synthetic N-formylated peptides as substrates in a continuous spectrophotometric assay. (Wei and Pei, Analytical Biochemistry 250:29-34 (1997)). A continuous spectrophotometric assay may be used to monitor plant peptide deformylase activity, i.e., to detect and quantify the enzyme product formed in the method of the invention. Alternatively, a discontinuous spectrophotometric assay may also be used.

The presence of peptide deformylase protein may be assessed using immunological methods, such as by using antibody directed to the protein or a part thereof, and by known enzymatic assays, such as peptide deformylase activity assays as described above. Coupled deformylase assays may also be used for measuring enzymatic activity and inhibition thereof as described by Rajagopalan et al., Biochemistry 36:13910-13918 (1997).

The invention also relates to a method of inhibiting the activity of plant peptide deformylase comprising exposing said peptide deformylase to an effective amount of an inhibitor of said peptide deformylase. An effective amount of an inhibitor is the concentration of the inhibitor that is required to reduce plant peptide deformylase activity.

The invention also relates to a method of identifying herbicides which comprises testing a candidate inhibitor in a peptide deformylase assay, and where a measurable reduction of plant peptide deformylase is observed, subjecting the candidate inhibitor to conventional test(s) to confirm the in vivo herbicidal activity.

A measurable reduction includes a reduction that is statistically significant, statistically significant being defined as the results from analysis of variance where the F-ratio, LSD (least significant difference), orthogonal/non-orthogonal comparison, or any other statistical technique for mean separation, that indicates the means are different at 0.05 or 0.01 level. In one embodiment of the invention, the measurable reduction is at least 10%.

Conventional tests for confirming in vivo herbicidal activity include, but are not limited to, detecting decreases in fresh weight, dry weight, chlorophyll, protein, and germination. Typical symptoms resulting from treatment of plant foliage with herbicides are cessation of growth followed by chlorosis and necrosis.

Although in vitro peptide deformylase assays will identify intrinsic herbicidal activity, it may in some cases be necessary to use conventional, tests to confirm the in vivo herbicidal activity. Accordingly, the invention further relates to a method of identifying potential herbicides that can be metabolized to an inhibitor of peptide deformylase in plants which comprises testing a compound in a peptide deformylase assay, and where a measurable reduction of plant peptide deformylase is observed, subjecting the compound to conventional test(s) to confirm the in vivo herbicidal activity.

Of course, those skilled in the art would appreciate that the invention encompasses herbicides identified by the methods of the invention. The invention also includes the use as a herbicide of a compound which is an inhibitor of plant peptide deformylase, with the proviso that the compound is not a general enzyme inhibitor.

Still further, the invention relates to a method of combating weeds comprising treating said weeds with a herbicide, wherein said herbicide is a compound which is an inhibitor of peptide deformylase in plants.

The invention also relates to a method of controlling vegetation comprising applying to plant foliage a herbicidally effective amount of an inhibitor of peptide deformylase.

Since bacterial peptide deformylase is a metallo hydrolase, compounds containing a metal ion chelating group are potential inhibitors of the enzyme. These compounds may also inhibit plant peptide deformylase and are encompassed with the scope of the present invention.

Examples of inhibitors of the invention include, but are not limited to, divalent metal chelators, dithiol compounds such as 1,2-ethanedithiol, 1,3-propanedithiol, 2,3-dimercapto-1-propanol, 2,3-dimercapto-1-propanol, 2,3-dimercapto-1-propanesulfonic acid and 1,5-pentanedithiol.

Also included are divalent metal-chelating agents such as 1,10-phenanthroline, 2-mercapto ethanol, glutathione, EDTA, thiophenol and thio-specific agents [p-(chloro mercuri)-benzoate] and iodoacetate.

Also included are 7,8 benzoquinoline, methyl 2-(sulfanylmethyl) hexanoate (TN) and imino[(5-methoxy-5-oxo-4-[2-sulfanylmethyl)-hexanoyl]amino pentyl) amino]methamine (TNR).

The inhibitors of the invention may be substrate analogue inhibitors such as thiophan (3-mercapto-2-benzylpropanoylglycine) and captopril (3-mercapto-2-methylpropanoyl proline), or other types of enzyme inhibitors known in the art. Such inhibitors may be designed and/or synthesized using methods known in the art, including transition-state-analogue chemistry, such as used by Pei et al. (Dept. of Chemistry, The Ohio State University, Columbus, Ohio).

Also included as inhibitors of the invention are peptide aldehydes, including those described by Durand et al., Archives Biochemistry and Biophysics, 367(2):297-302 (1999), as inhibitors of bacterial peptide deformylase.

Given the absence of a protein crystal structure for plant peptide deformylase, which has a specific and unique amino acid sequence different from any previously described peptide deformylase, inhibitors of the invention may also include novel compounds.

Those of skill in the art would recognize that the inhibitors of the invention may be used as non-selective herbicides.

The importance of peptide deformylase to the well being of plants has been demonstrated by the potent herbicidal effects obtained when the enzyme is inhibited. Recent studies have shown the fungal product, actinonin, to be an inhibitor of bacterial peptide deformylase (Chen et al., Biochemistry, 39(6):1256-1263 (2000). A role for peptide deformylase in plant growth was suggested from analysis of the effects of the application of actinonin, on the growth of pea plants.

As shown in FIG. 5 and Example 5, observable alterations in plant growth, i.e., stunting and yellowing of pea plants, were evident in the presence of actinonin. Nearly complete inhibition of peptide deformylase activity was observed in an in vitro peptide deformlyase inhibition assay. (FIG. 8 and Example 8) This data establishes that the potent herbicidal activity of actinonin is due to inhibition of peptide deformylase. This mode of action has not previously been described for herbicides.

Herbicidal Compositions

The inhibitors of the invention may be formulated as herbicidal compositions. A herbicidal composition can be formulated in a conventional manner using an inhibitor of plant peptide deformylase polypeptide, as an active ingredient, together with suitable carriers, diluents, emulsifiers and/or dispersants. The herbicidal composition can be formulated as a wettable powder, pellets, granules or dust or as a liquid formulation with aqueous or non-aqueous solvents as a foam, gel, suspension, or concentrate.

A method for controlling the growth of weeds in accordance with this invention can comprise applying (e.g., spraying), to a locus (area) to be protected, an herbicidally effective amount of an inhibitor of plant peptide deformylase polynucleotide and/or polypeptide of the invention. The locus to be protected can include, for example, the habitat of the growing vegetation or an area where vegetation is to be grown.

It will be appreciated that to effect control of undesired plant vegetation pursuant to this invention recourse may be had to herbicidal activity whereby undesired vegetation is killed and/or to plant growth regulant activity whereby the further growth of the vegetation is stunted, inhibited and/or slowed without actually killing all of the undesired vegetation treated with the composition.

The herbicidal and growth regulating compositions of the invention include aqueous concentrates which can be shipped and stored until diluted with more water on site to produce the final solution for application to the foliage as by spraying. Likewise the herbicidal and the plant growth regulant compositions of this invention include the more dilute aqueous solutions for use in application to the foliage. These more dilute aqueous solutions are preferably formed simply by suitably diluting a concentrate of this invention with water (if a powder or granular concentrate) or with more water (if a liquid concentrate) to achieve the appropriate dosage, but alternatively, can be formed on site by mixing the ingredients separately and/or in sub-combinations with sufficient water on site to achieve the appropriate dosage. Use of the solid or liquid concentrates of this invention is preferable as it is a much simpler operation and minimizes the possibility of blending errors. Moreover, if desired, other components can be introduced into the final solution at the time the concentrate is blended with water to form the diluted solution for application to the foliage.

The herbicides of the invention may be applied with a surfactant in order to improve leaf wetting and assist in penetration of the active ingredient into the leaf. The surfactant is typically an inert ingredient in the formulation. Surfactants of virtually any class may be used. Examples of surfactants which may be useful include StilWet, Tween, polyalkylene glycols (such as polyethylene glycols), alkanolamides, betaine derivatives, ethoxylated propoxylated block copolymers, glycerol esters, glycol esters, imidazolines and imidazoline derivatives, lanolin derivatives, lecithin derivatives, tertiary or quaternary polyoxyalkylene alkylamines, polyoxyalkylene and non-polyoxyalkylene alkylamine oxides, polyoxyalkylene alkylethers, polyoxyalkylene alkylarylethers, polyoxyalkylene alkylesters, alkoxylated and non-alkoxylated sorbitan esters, alkyl glycosides, alkyl polyglycosides, sucrose esters, sucrose glycerides, alkyl sulfates or phosphates, olefin sulfonates, alkylaryl sulfonates, polyoxyalkylene alkylether sulfates or phosphates, sulfosuccinate derivatives, sulfosuccinamates, taurates, sulfates and sulfonates of oils, fatty acids, alcohols, alkoxylated alcohols, fatty esters and aromatic derivatives, mixtures thereof and the like. The surfactant is preferably StilWet. Those skilled in the art will recognize that other surfactants not included above may also useful.

Effective concentrations of the herbicides and herbicidal compositions and formulations of the invention may be readily determined using the methods described herein wherein preparations are bioassayed for their inhibitory ability to known preparations of peptide deformylase. In order to control growth of vegetation, the compositions should contain the amount of inhibitor required to effectuate plant growth regulant activity whereby the further growth of the vegetation is stunted, inhibited and/or slowed without actually killing all of the undesired vegetation treated with the composition.

Antagonists

Peptide deformylase polypeptides of the invention may be used to assess the binding of small molecule substrates and ligands in, for example, cells, cell-free preparations, chemical libraries, and natural product mixtures. These substrates and ligands may be natural substrates and ligands or may be structural or functional mimetics. See, e.g., Coligan et al., Current Protocols in Immunology 1(2): Chapter 5 (1991).

Accordingly, the invention provides a method of screening compounds to identify those which block (antagonist) the action of peptide deformylase polypeptides. The method of screening may involve high-throughput techniques. For example, to screen for antagonists, a synthetic reaction mix, a cellular compartment, such as a membrane, cell envelope or cell wall, or a preparation of any thereof, comprising a peptide deformylase polypeptide and a labeled substrate or ligand of such polypeptide is incubated in the absence or the presence of a candidate molecule that may be a peptide deformylase antagonist. The ability of the candidate molecule to antagonize the peptide deformylase polypeptide is reflected in decreased binding of the labeled ligand or decreased production of product from such substrate. Molecules that bind gratuitously, i.e., without inducing the effects of a peptide deformylase polypeptide are most likely to be good antagonists. Detection of the rate or level of production of product from substrate may be enhanced by using a reporter system. Reporter systems that may be useful in this regard include but are not limited to colorimetric labeled substrate converted into product, a reporter gene that is responsive to changes in peptide deformylase polynucleotide or polypeptide activity, and binding assays known in the art.

Another example of an assay for peptide deformylase antagonists is a competitive assay that combines peptide deformylase and a potential antagonist with peptide deformylase-binding molecules, recombinant peptide deformylase binding molecules, natural substrates or ligands, or substrate or ligand mimetics, under appropriate conditions for a competitive inhibition assay. Peptide deformylase can be labeled, such as by radioactivity or a calorimetric compound, such that the number of peptide deformylase molecules bound to a binding molecule or converted to product can be determined accurately to assess the effectiveness of the potential antagonist.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that binds the same sites on a binding molecule, such as a binding molecule, without inducing peptide deformylase-induced activities, thereby preventing the action of peptide deformylase by excluding deformylase from binding.

Potential antagonists also include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, J. Neurochem. 56:560 (1991); Oligodeoxynucleotides as Antisense Inhibitors of Gene Expression, CRC Press, Boca Raton, Fla. (1988), for a description of these molecules). Preferred potential antagonists include compounds related to and variants of peptide deformylase.

Antibodies

The present invention further relates to an antibody directed against plant peptide deformylase. In this regard, the polypeptides of the invention or variants thereof, or cells expressing them can be used as an antigen to produce antibodies immunospecific for such polypeptides. "Antibodies" as used herein includes monoclonal and polyclonal antibodies, chimeric, single chain, simianized antibodies and humanized antibodies, as well as Fab fragments, including the products of an Fab immunoglobulin expression library.

Antibodies generated against the polypeptides of the invention can be obtained by administering the polypeptides or epitope-bearing fragments, analogues or cells to an animal using routine protocols. For preparation of monoclonal antibodies, any technique known in the art that provides antibodies produced by continuous cell line cultures can be used. Examples include various techniques, such as those in Kohler, G. and Milstein, C., Nature 256:495-497 (1975); Kozbor et al., Immunology Today 4:72 (1983); Cole et al., Monoclonal Antibodies and Cancer Therapy, Alan R. Liss, Inc., pg. 77-96 (1985).

Techniques for the production of single chain antibodies (U.S. Pat. No. 4,946,778) can be adapted to produce single chain antibodies to polypeptides of this invention.

Alternatively phage display technology may be utilized to select antibody genes with binding activities towards the polypeptide either from repertoires of PCR amplified v-genes of lymphocytes from humans screened for possessing antidef or from naive libraries (McCafferty, J. et al., Nature 348: 552-554 (1990); Marks, J. et al., Biotechnology 10:779-783 (1992)). The affinity of these antibodies can also be improved by chain shuffling (Clackson, T. et al., Nature 352:624-628 (1991)).

If two antigen binding domains are present each domain may be directed against a different epitope—termed 'bispecific' antibodies.

The above-described antibodies may be employed to isolate or to identify clones expressing plant peptide deformylase polypeptides and to purify the polypeptides by affinity chromatography.

Transgenics

As with other broad spectrum herbicides, such as glyphosate, overexpression or expression of altered forms of peptide deformylase in plants using conventional transformation techniques might generate plants resistant to the adverse effects of peptide deformylase inhibitors.

Thus, the invention further relates to a transgenic plant, wherein said plant is engineered to be resistant to inhibitors of plant peptide deformylase. In a further aspect, the present invention relates to a recombinant or transgenic plant transformed with a peptide deformylase gene such that the deformylase is over expressed.

Additionally, sense and antisense forms of the *Arabidopsis*, as well as bacterial peptide deformylases, may be engineered into plant transformation vectors for the construction of transgenic plants with up- and down-regulated levels of peptide deformylase, for testing as resistant and susceptible plant species to peptide deformylase inhibitors.

A variety of techniques may be used to introduce foreign genes into plant cells. One common method used to introduce foreign genes into plant cells is transformation with disarmed *Agrobacterium*, a relatively benign natural plant pathogen. *Agrobacterium* actively mediates transformation events—the integration of a gene providing a desired phenotypic trait—as part of the natural process it utilizes when it infects a plant cell. Methods for transferring foreign genes into plant cells and the subsequent expression of the inserted genes in plants regenerated from transformed cells are well known in the art. (See, e.g., De Block et al., The EMBO Journal 3:1681 (1984); Horsch et al. Science 227:1229 (1985); and C. L. Kado (Crit. Rev. Plant. Sci. 10:1 (1991)).

The technique known as microprojectile bombardment has been successfully used to introduce genes encoding new genetic traits into a number of crop plants, including cotton, maize, tobacco, sunflowers, soybeans and certain vegetables. (See for example, U.S. Pat. No. 4,945,050, issued to Sanford; Sanford et al., Trends in Biotechnology 6:299 (1988); Sanford et al., Part. Sci. Technol. 5:27 (1988); J. J. Finer and M. D. McMullen, Plant Cell Reports 8:586-589 (1990); and Gordon-Kamm, The Plant Cell 2:603 (1990)).

Organogenesis, the development of plantlets from specific plant structures such as leaf disks or root tips, has been used to regenerate plants following transformation. An alternative approach has been described by Feldman, who has shown that it is feasible to vacuum infiltrate the floral meristems of small plants, or in the case of *Arabidopsis*, the entire plant with *Agrobacterium* and obtain transgenic progeny. See K. A. Feldman et al., "*Agrobacterium*-Mediated Transformation of Germinating Seeds of *Arabidopsis thaliana*: A Non-Tissue Culture Approach," Mol. Gen. Genet. 308:1-9 (1987).

The use of specific herbicides relies on differential uptake and/or metabolism between weed and crop plant or on application of the herbicide before planting in a field. Herbicide tolerant plants/crops can be created by either of three strategies: i) increasing the level of the target enzyme for the herbicide (See, e.g. U.S. Pat. No. 4,940,835, issued to Shah et al.), ii) expressing a mutant enzyme that is not affected by the compound (Comai, L., et al., Nature 317:741-744 (1985)), iii) expressing an enzyme that detoxifies the herbicide (De Block, M., et al., EMBO J. 6:2513-2518 (1987), Stalker, D. M., et al., Science 242:419-423 (1988)), or iv) knocking out or antisense down regulation of the plant formyl transferase gene.

With the first approach, i), a cDNA encoding plant peptide deformylase may be transferred into a plant in order to over express the deformylase enzyme. Over expression of the enzyme allows the transgenic plants to grow in the presence of higher levels of the herbicide that kills the wild-type or non-transgenic plants.

With approach ii), herbicide-tolerant plants are created by use of mutant forms of the plant or bacterial peptide deformylase that are less sensitive to inhibition by the herbicide. Genes encoding these mutants may be cloned and expressed in plants. The transgenic plants should exhibit tolerance to levels of herbicide that kill wild-type plants.

Plant peptide deformylase is synthesized in the cytoplasm and translocated to the chloroplast by proteins that recognize and bind the amino-terminal region (transit peptide). In order to target the bacterial peptide deformylase to chloroplasts, a gene segment encoding the plant transit peptide may be fused to the coding sequence for the bacterial enzyme.

The third approach for creating herbicide-tolerant plants employs transgenic expression of enzymes that convert the herbicide to a form that is not toxic to the plant. Some plants have their own detoxifying systems for certain herbicides. Some bacteria have been found that naturally degrade herbicides.

The fourth approach for creating herbicide tolerant plants draws from bacterial systems where knock-out of the formyl transferase gene, which codes for the formyl transferase enzyme responsible for the formation of N-formylmethionine, results in the formation of a cell line that while slow in growth, is no longer susceptible to peptide deformylase inhibitors or mutations in the peptide deformylase gene.

In order to express all or an effective part of the DNA sequence encoding a peptide deformylase protein of this invention in E. coli and in plants, suitable restriction sites can be introduced, flanking the DNA sequence. This can be accomplished by site-directed mutagenesis, using well-known procedures (Stanssens et al., Nucleic Acids Research 12:4441-4454 (1989); White et al., Trends in Genet. 5:185-189 (1989)). In order to obtain improved expression in plants, the codon usage of the peptide deformylase gene or effective peptide deformylase gene part of this invention can be modified to form an equivalent, modified or artificial gene or gene part, or gene parts can be inserted in the chloroplast genome and expressed there using a chloroplast-active promoter (e.g., McBride et al., Bio/Technology 13:362 (1995)). For obtaining enhanced expression in monocot plants such as corn, a monocot intron also can be added to the chimeric gene, and the DNA sequence of the peptide deformylase gene or part thereof can be further changed in a translationally neutral manner, to modify possibly inhibitory DNA sequences present in the gene or gene part by means of site-directed intron insertion and/or by introducing changes to the codon usage, e.g., adapting the codon usage to that most preferred by the specific plant (Murray et al., Nucleic Acids Research 17(2):477-498 (1989)) without changing significantly the encoded amino acid sequence.

Furthermore, the binding properties of the peptide deformylase proteins of the invention can be evaluated, using methods known in the art.

The peptide deformylase gene part or its equivalent, preferably a peptide deformylase chimeric gene, encoding a variant of the peptide deformylase, can be stably inserted in a conventional manner into the nuclear genome of a single plant cell, and the transformed plant cell can be used in a conventional manner to produce a transformed plant that is resistant to a peptide deformylase inhibitor.

In this regard, a disarmed Ti-plasmid, containing the peptide deformylase gene or part thereof, in Agrobacterium tumefaciens can be used to transform the plant cell, and thereafter, a transformed plant can be regenerated from the transformed plant cell using the procedures described. For example, preferred Ti-plasmid vectors each contain the peptide deformylase gene or part thereof between the border sequences, or at least located to the left of the right border sequence, of the T-DNA of the Ti-plasmid. Of course, other types of vectors can be used to transform the plant cell, using procedures such as direct gene transfer, pollen-mediated transformation, plant RNA virus-mediated transformation, liposome-mediated transformation, and other methods such as the recently described methods for transforming certain lines of corn (Fromm et al., Bio/Technology 8:833-839 (1990); Gordon-Kamm et al., The Plant Cell 2:603-618 (1990)) and rice (Shimamoto et al., Nature 338:274-276 (1989); Datta et al., Bio/Technology 8:736-740 (1990)) and the recently described method for transforming monocots generally (PCT publication WO 92/09696).

The resulting transformed plant can be used in a conventional plant breeding scheme to produce more transformed plants with the same characteristics or to introduce the peptide deformylase gene part in other varieties of the same or related plant species. Seeds, which are obtained from the transformed plants, contain the peptide deformylase gene part as a stable genomic insert. Cells of the transformed plant can be cultured in a conventional manner to produce the peptide deformylase protein which can be recovered for use in methods of identifying herbicidal compounds.

The peptide deformylase gene or gene part, preferably the truncated peptide deformylase gene, may be inserted in a plant cell genome so that the inserted gene is downstream (i.e., 3') of, and under the control of, a promoter which can direct the expression of the gene part in the plant cell. This is preferably accomplished by inserting the peptide deformylase chimeric gene in the plant cell genome; particularly in the nuclear genome. Preferred promoters include: the strong constitutive 35S promoters (the "35S promoters") of the cauliflower mosaic virus (CaMV) of isolates CM 1841 (Gardner et al., Nucleic Acids Research 9:2871-2887 (1981)), CabbB-S (Franck et al., Cell 21:285-294 (1980)) and CabbB-J1 (Hull and Howell, Virology 86:482-493 (1987)); promoters from the ubiquitin family (e.g., the maize ubiquitin promoter of Christensen et al., Plant Mol. Biol. 18:675-689 (1992), see also Cornejo et al., Plant Mol. Biol. 23:567-581 (1993)), the gos2 promoter (de Pater et al., 1992), the emu promoter (Last et al., Theor. Appl. Genet. 81:581-588 (1990)), rice actin promoters such as the promoter described by Zhang et al., The Plant Cell 3:1155-1165 (1991); and the TR1' promoter and the TR2' promoter (the "TR1' promoter" and the "T2' promoter", respectively) which drive the expression of the 1' and 2' genes, respectively, of the T-DNA (Velten et al., EMBO J. 3:2723-2730 (1984)).

Alternatively, a promoter can be utilized which is not constitutive but rather is specific for one or more tissues or organs of the plant (e.g., leaves and/or roots) whereby the inserted peptide deformylase gene part is expressed only in cells of the specific tissue(s) or organ(s). For example, the peptide deformylase gene part could be selectively expressed in the leaves of a plant (e.g., corn, cotton) by placing the gene part under the control of a light-inducible promoter such as the promoter of the ribulose-1,5-bisphosphate carboxylase small subunit gene of the plant itself or of another plant such as pea as disclosed in U.S. Pat. No. 5,254,799. Another alternative is to use a promoter whose expression is inducible (e.g., by temperature or chemical factors).

The peptide deformylase gene or part thereof may be inserted in the plant genome so that the inserted gene part is upstream (i.e., 5') of suitable 3' end transcription regulation signals (i.e., transcript formation and polyadenylation signals). This is preferably accomplished by inserting the peptide deformylase chimeric gene in the plant cell genome. Preferred polyadenylation and transcript formation signals include those of the octopine synthase gene (Gielen et al., EMBO J. 3:835-845 (1984)) and the T-DNA gene 7 (Velten and Schell, Nucleic Acids Research 13:6981-6998 (1985)), which act as 3'-untranslated DNA sequences in transformed plant cells.

The peptide deformylase gene or part thereof can optionally be inserted in the plant genome as a hybrid gene (U.S. Pat. No. 5,254,799; Vaeck et al., J. Econ. Entomol 55:140 (1962)) under the control of the same promoter as a selectable marker gene, such as the neo gene (EP 0 242 236) encoding kanamycin resistance, so that the plant expresses a fusion protein.

GLOSSARY

The following definitions are provided to facilitate understanding of certain terms used frequently herein.

A "host cell" is a cell which has been transformed or transfected, or is capable of transformation or transfection by an exogenous polynucleotide sequence.

"Homologous" or "substantial identity," when referring to nucleic acids as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence. The percentage of sequence identity is calculated excluding small deletions or additions which total less than 25 percent of the reference sequence. "Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990). As an illustration, by a polynucleotide having a nucleotide sequence having at least, for example, 95% "identity" to a reference nucleotide sequence, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having an amino acid sequence having at least, for example, 95% identity to a reference amino acid sequence, it is intended that the amino acid sequence of the polypeptide is identical to the reference sequence except that the polypeptide sequence may include up to five amino acid alterations per each 100 amino acids of the reference amino acid. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence. The reference sequence in the instant case may be the sequence of Atdef1, Atdef2, AtDEF1, or AtDEF2.

"Isolated" means altered "by the hand of man" from its natural state, i.e., if it occurs in nature, it has been changed or removed from its original environment, or both. For example, a polynucleotide or a polypeptide naturally present in a living organism is not "isolated", but the same polynucleotide or polypeptide separated from the coexisting materials of its natural state is "isolated", as the term is employed herein.

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded-regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini.

Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, transfer-RNA mediated addition of amino acids to proteins, such as arginylation, and ubiquitination. (See, for example, Proteins-structure And Molecular Properties, 2nd Ed., T. E. Creighton, W. H. Freeman and Company, New York (1993) and Wold, F., Posttranslational Protein Modifications: Perspectives and Prospects, pgs. 1-12 in Posttranslational Covalent Modification of Proteins, B. C. Johnson, Ed., Academic Press, New York (1983); Seifter et al., Meth. Enzymol. 182:626-646 (1990) and Rattan et al., Protein Synthesis Posttranslational Modifications and Aging, Ann. N.Y. Acad. Sci. 663:48-62 (1992)). Polypeptides may be branched or cyclic, with or without branching. Cyclic, branched and branched circular polypeptides may result from post-translational natural processes and may be made by entirely synthetic methods, as well. The terms "peptide", "polypeptide" or "protein" are used interchangeably herein.

"Stringent hybridization conditions" refers to conditions which permit hybridization between polynucleotides. Stringent conditions can be defined by salt concentration, the concentration of organic solvent (e.g., formamide), temperature, and other conditions well known in the art. In particular, stringency can be increased by reducing the concentration of salt, increasing the concentration of formamide, or raising the hybridization temperature. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and most preferably at least about 50% formamide. Stringent temperature conditions will ordinarily include temperatures of at least about 30° C., more preferably of at least about 37° C. and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. The washing steps which follow hybridization can also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include temperature of at least about 25° C., more preferably of at least about 42° C., and most preferably of at least about 68° C. will occur at 42° C. in 15 mM NaCl, 1.5 mM trisodium citrate, and 0.1% SDS. Additional variations on these conditions will be readily apparent to those skilled in the art.

"Variant(s)" as the term is used herein, is a polynucleotide or polypeptide that differs from a reference polynucleotide or polypeptide respectively, but retains essential properties. A typical variant of a polynucleotide differs in nucleotide sequence from another reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

All references cited in the present application are expressly incorporated by reference herein.

The following examples are provided for illustrative purposes and are not intended to limit the scope of the invention as claimed herein. Any variations in the exemplified compositions and methods that occur to the skilled artisan are intended to fall within the scope of the present invention.

EXAMPLE 1

Identification and Isolation of an *Arabidopsis* Peptide Deformylase Gene (Atdef1)

The *Arabidopsis thaliana* genome sequencing project recently annotated a gene (AC007591; F9L1.35 at www.ncbi.nlm.nih.gov;) as a putative peptide deformylase based on substantial homology to *Chlamydia pneumoniae* (AE001687) protein. An identifiable chloroplast targeting sequence was also identified. The predicted protein sequence was analyzed using the ChloroP program (Emanuelsson et al., Protein Science 8:978-984 (1999)), which revealed a putative transit peptide of 50 amino acids. (See FIGS. 1A and 1B.)

Construction of a Peptide Deformylase Clone (Atdef1)

Experiments were initiated to amplify *Arabidopsis thaliana* peptide deformylase complementary DNA (cDNA) using Reverse Transcriptase-Polymerase Chain Reaction (RT-PCR).

Isolation of *Arabidopsis thaliana* RNA

Total RNA was isolated using TRIzol™ reagent from GIBCO BRL, following the manufacturer's protocol. Briefly, the procedure was as follows: 0.5 gm *Arabidopsis thaliana* cv. Columbia leaves were homogenized in 5 ml of TRIzol™ reagent with a Polytron homogenizer for 10-15 seconds using a power setting of 5. Following a 5 minute room temperature incubation, 1.0 ml of chloroform was added. The samples were mixed and centrifuged at 12,000×g for 15 minutes at 4° C. Following centrifugation, the aqueous phase was removed and the RNA precipitated with 2.5 ml of isopropyl alcohol. The precipitate was collected by centrifugation at 12,000×g for 10 minutes at 4° C. The RNA pellet was washed with 1.0 ml of 70% ethanol, dried briefly, and resuspended in DEPC-treated water.

First Strand cDNA Synthesis

First strand cDNA was prepared from RNA isolated from *Arabidopsis thaliana* cells using gene specific primers RLH 146 and 147 having the sequence 5' TTG TCG ACA AAA GCC GGT TGG 3' (SEQ ID NO: 1) and 5' TCA TTG AGG TCC GAG CTT AG 3' (SEQ ID NO: 2), respectively. The reverse transcription reaction was carried out in a 20 ul reaction volume containing 4 ul of RNA (150 ng/ml), 1.5 ul of 3' antisense oligo (likely RLH 147) (10 uM stock diluted to a final concentration of 0.75 uM), 8.5 ul of water, 1 ul of 20 mM each dATP, dGTP, dCTP, dTTP (final concentration of 1 mM), 2 ul of MgCl$_2$ (to final concentration of 5 mM), 2 ul of PCR buffer (10×200 mM Tris-HCl, pH 8.4, 500 mM KCl) used according to the manufacturer's instructions (Gibco BRL™ Life Technologies™) and 200 units of MMLV reverse transcriptase (Gibco BRL™ Life Technologies™.) for 30 minutes at 42° C. in a RoboCycler™ Gradient 40 Temperature Cycler (Stratagene™.; La Jolla, Calif., USA 92037). This reaction was terminated by incubation at 99° C for 5 minutes and subsequently cooled to 6° C.

Polymerase Chain Reaction

The first strand cDNA was used as a PCR template. RoboCycler® Gradient 40 Temperature Cycler was used with the following temperature regime:

| | |
|---|---|
| 1 cycle | 3 minutes 94° C. |
| 35 cycles | 1 minute 94° C., 1 minute 50° C., 1 minute 72° C. |
| 1 cycle | 10 minutes 72° C. |

Figure 2:
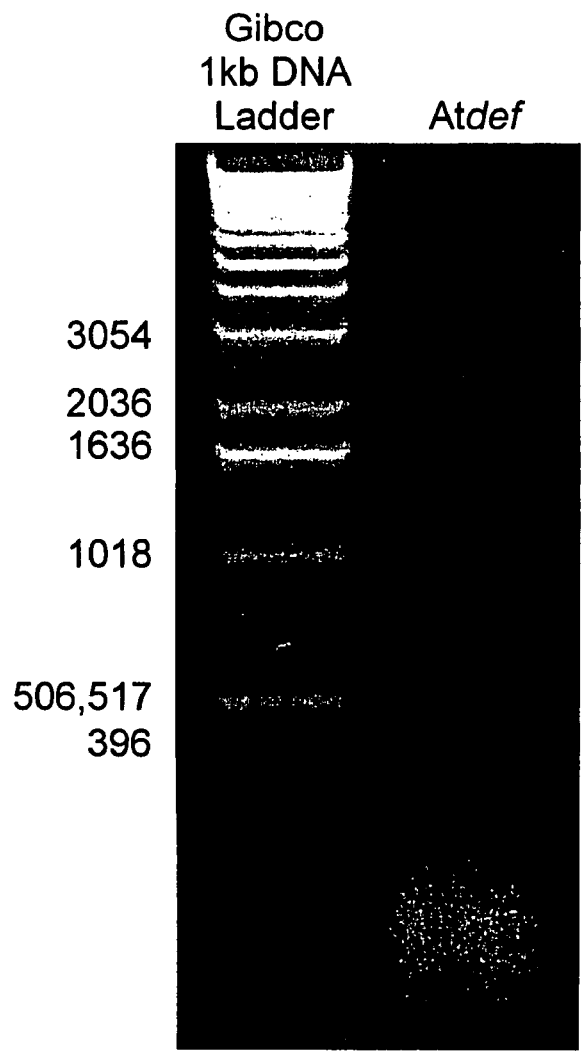
FIG. 2 is a gel showing an amplicon of the expected size, 630 bp, which was created when *Arabidopsis* RNA was reversed-transcribed and Atdef1 amplified with gene specific primers (RLH 146X147).

The reaction product was analyzed by adding an aliquot of the reaction mixture to loading dye and loading into wells of a 1% TAE gel and subjecting the gel to electrophoresis. (FIG. 2.)

Ligation to pCR®2.1 Vector

The amplicon of the expected size, 630 bp, was cloned into pCR®2.1 TA-vector (Invitrogen). (See FIG. 2.) The 10 μl ligation reaction mixture contained 1-2 μl of PCR product, 1 μl of 10× ligation buffer, 2 μl of pCR®2.1 vector (25 ng/μl), sterile water to a total volume of 10 μl. One microliter of T4 DNA Ligase (4.0 Weiss units) was added to the reaction mixture and the ligation reaction was incubated at 14° C. for a 14-16 hours.

Transformation

To each vial of One Shot™ INVαF' competent cells (Invitrogen) were added 2 μl of 0.5 M β-mercaptoethanol and the sample was mixed by stirring gently with a pipette tip. Afterwards, 2 μl of the TA Cloning® reaction (ligation reaction) were added into a vial of One Shot™ cells and mixed gently. The mixture was incubated on ice for 30 minutes. The cells were subjected to heat shock for 30 seconds at 42° C. without shaking. The cells were then immediately transferred to ice and incubated for 2 minutes. Next, 250 μl of room temperature SOC medium (formulation per liter: 20 g tryptone, 5 g yeast extract, 0.5 g NaCl, 0.95 g MgCl$_2$, and 20 mM glucose) were added. The tube was capped tightly and shaken horizontally at 37° C. for 60 minutes.

Approximately, 50-100 μl from each transformation were spread on a prewarmed LB-agar plate containing the 100 μg/ml ampicillin and X-Gal, and the inverted plates were incubated overnight at 37° C. Approximately 10 white or light blue colonies were picked for analysis.

Sequence Analysis

Determination of the DNA sequence of the insert confirmed that this plasmid had the expected and desired structure. Sequence determinations were carried out by the dideoxynucleotide chain termination procedure (Sanger et al. (1977) Proc. Natl. Acad. Sci. USA 74:8073-8077), with an automated fluorescence-based system (Applied Biosystems, Foster City, Calif.). The DNA sequence of the Atdef1 insert is identical to the deduced [computer generated] cDNA sequence of gene AC 007591.2 in the *Arabidopsis* genome sequence.

EXAMPLE 2

Expression and Purification of *Arabidopsis thaliana* Peptide Deformylase (AtDEF1)

Cloning into pLEX

Restriction Endonuclease Digestion

The peptide deformylase gene (from Example I) was digested with NdeI and XhoI and ligated into pLEX (Invitrogen) that had been digested with NdeI and XhoI restriction endonucleases according to the manufacturer's protocol (PL Expression system version D 180129).

Ligation to pLEX

The 10 µl ligation reaction contained 1 µl of linearized pLEX vector (50-200 ng), 2 µl of linearized insert (5-200 ng), 1 µl of 10× ligation Buffer (should have ATP), sterile water to 9 µl, and 1 µl of T4 DNA Ligase (0.5 Weiss Units). The reaction mixture was incubated for 12-16 hours at 15° C.

Transformation

Three to five microliters of the ligation reaction were added to a separate tube of competent cells (GI724) and mixed gently with a pipette tip (without PIPETTING UP AND DOWN). The tubes were incubated on ice for 30 minutes. All tubes were then transferred to 42° C. water bath and incubated for 90 seconds, then placed on ice for 1-2 minutes. Then, 800 µl of room temperature SOC medium were added to each tube and the tubes were shaken at 225 rpm for 45 minutes at 37° C. Afterwards, 100 µl and 300 µl of each transformation mix were plated on RMG-Amp (formulation of RMG per liter: 6 g $Na_2HPO_4$, 3 g $KH_2PO_4$, 0.5 g NaCl, 1 g $NH_4Cl$, 20 g Casamino Acids, 5 g glucose, 20.33 mg $MgCl_2$, 15 g Agar plus 100 µg/ml ampicillin) transformation plates, the liquid was allowed to dry, and the inverted plates were incubated at 30° C. overnight.

Plates were removed from the incubator and 10 transformants were picked and inoculated into 2-5 ml of RM medium (formulation per liter: 6 g $Na_2HPO_4$, 3 g $KH_2PO_4$, 0.5 g NaCl, 1 g $NH_4Cl$, 20 g Casamino Acids, 10 ml glycerol, 20.33 mg $MgCl_2$ with 100 µg/ml ampicillin). The inoculants were incubated at 30° C. overnight.

Mini-plasmid Preparation

Plasmid DNA was isolated by miniprep for restriction analysis and sequencing. The miniprep DNA isolation was conducted using a small-scale procedure (Sambrook, J., et al. (1989) Molecular Cloning: A Laboratory Manual, $2^{nd}$ Ed. Cold Spring Harbor Laboratory Press, NY, USA, pages 1.25-1.28), resuspending the final DNA pellet in 20 µl 10 mM Tris, pH 8.0 with 0.1 µg/ml RNase A. The desired clone was purified by streaking for single colonies on RMG-Amp plates before making glycerol stocks.

Sequence Analysis

To confirm the peptide deformylase DNA sequence was in frame with the initiating ATG, the construct was sequenced using the pLEX Forward Sequencing Primer and the AspA Reverse Sequencing Primer (Invitrogen). Sequence determinations were carried out by the dideoxynucleotide chain termination procedure Sanger et al. (1977) Proc. Natl. Acad. Sci. USA 74:8073-8077) with an automated fluorescence-based system (Applied Biosystems, Foster City, Calif.).

Expression and Isolation of AtDEF1

On Day 1, the clone of interest was streaked out on a RMG-Amp plate with 100 µg/ml ampicillin and grown at 30° C. until single colonies were visible (12-16 hours).

On Day 2 and using a single colony from the plate from Day 1, 1 ml of RM medium containing 100 µg/ml ampicillin was inoculated and incubated at 30° C. at 200-225 rpm in a shaking incubator overnight.

On Day 3, 10 ml of fresh Induction Medium was inoculated in a 25 ml culture flask to an $OD_{550}$ of 0.1 using the overnight culture. This culture was grown at 30° C. to an $OD_{550}$ of 0.5 (approximately 2-3 hours). When an $OD_{550}$ of 0.5 was reached, a 1 ml aliquot was transferred to a microcentrifuge tube labeled "t=0", and the tube was centrifuged for 2-3 minutes at maximum speed to pellet the cells. This is the zero time sample. The supernatant was decanted and the cell pellet was frozen at −20° C. until ready to assay. The cell culture was returned to the incubator.

To the cell culture, tryptophan was added to a final concentration of 100 µg/ml using the 10 mg/ml stock solution included in the kit. The culture was transferred to 37° C. and incubated with shaking (200-225 rpm).

At time t=1 hour, the $OD_{550}$ was read and recorded. Then, a 1 ml sample was taken and placed into the microcentrifuge tube labeled "t=1". The cell culture was returned to the incubator to continue growing. The 1 ml sample was centrifuged at maximum speed for 2-3 minutes, the supernatant decanted, and the cell pellet frozen at −20° C. This was repeated at t=2, 3, and 4 hours.

On Day 4, the five samples were removed from the freezer and placed on ice. Each cell pellet was resuspended in 500 µl cold (+4° C.) TE Buffer, pH 7.5 and kept on ice. Using a hand-held sonicator with a micro-tip, each sample was sonicated one at a time with two or three 10 second bursts. The lysate was subjected to flash freezing in a dry ice/ethanol bath.

The lysates were quickly thawed at 37° C. and two more rapid sonication-freeze-thaw cycles were performed. Steps 3 and 4 were repeated until three sonication-freeze-thaw cycles were completed for all samples. After the last thaw, all tubes were centrifuged at maximum speed for 5-10 minutes at +4° C. to pellet cell debris and insoluble matter.

Peptide deformylase protein expressed in bacteria were synthesized as insoluble inclusion bodies, which can be isolated rather quickly (Paulsen et al. 1990; Waegemann and Soll, Methods in Cell Biology 50:255-267)). The bacteria were harvested by centrifugation (7000×g for 5 minutes) and resuspended in cold lysis buffer (50 mM Tris-HCl, pH 8, 25% (w/v) sucrose, 1 mM EDTA). Lysozyme was added to a final concentration of 2 mg/ml and the mixture was incubated for 30 minutes on ice. After addition of $MgCl_2$ (0.5 mM) and $MnCl_2$ (0.05 mM) the culture was treated with DNase I (40 µg/ml) for another 30 minutes on ice. Next, 2 volumes of cold detergent buffer (20 mM Tris-HCl, pH 7.5, 200 mM NaCl, 1% (w/v) deoxycholate, 1% (w/v) Nonidet P-40, 2 mM EDTA, 10 mM 2-mercaptoethanol) were added and mixed very carefully and extensively. After centrifugation (7000×g for 10 minutes) the supernatant was removed and the pellet was resuspended in cold Triton buffer (20 mM Tris-HCl, pH 7.5; 0.5% (v/v) Triton-X-100, 1 mM EDTA, 10 mM 2-mercaptoethanol). The sample was mixed well and centrifuged as above. The pellet was washed at least once more with Triton buffer until it appeared white. The pellet was washed once with cold Tris buffer (50 mM Tris-HCl, pH 7.6; 1 mM EDTA; 10 mM DTT). The collected inclusion bodies were finally resuspended in Tris buffer and stored as a suspension in 50 µl at −80° C. The inclusion bodies had to be solubilized with 6 M guanidine-HCl prior to the in vitro chloroplast import experiment.

EXAMPLE 3

In vitro Chloroplast Import of Peptide Deformylase

Although signal peptides vary in amino acid sequence and length, the tendencies for certain classes of amino acids as well as semi-conserved cleavage sites have facilitated computer modeling and prediction of signal sequences within a putative nuclear-encoded chloroplast protein. A neural network based predictor has recently been developed that discriminates transit peptide sequences from non-transit peptide sequences with high sensitivity and specificity. (Emanuelsson et al., Protein Science 8:978-984 (1999)).

The *Arabidpsis thaliana* peptide deformylase predicted protein sequence was analyzed using the neural network based predictor (Emanuelsson et al. Protein Science (1999) 8:978-984) ChloroP program, which predicted a signal peptide of 50 amino acids with a cleavage site between amino acids 50 and 51. Since signal peptides are capable of mediating precise chloroplast targeting and import, in vitro chloroplast import experiments were conducted using the peptide deformylase protein. The peptide deformylase protein would be predicted to function in the chloroplast due to it's prokaryotic lineage. Considering the difficulty in isolating an appreciable amount of chloroplast from young *Arabidopsis* plants, import studies were conducted using pea chloroplasts, which have been extensively used to study import of a wide variety of other precursor proteins.

Figure 3:
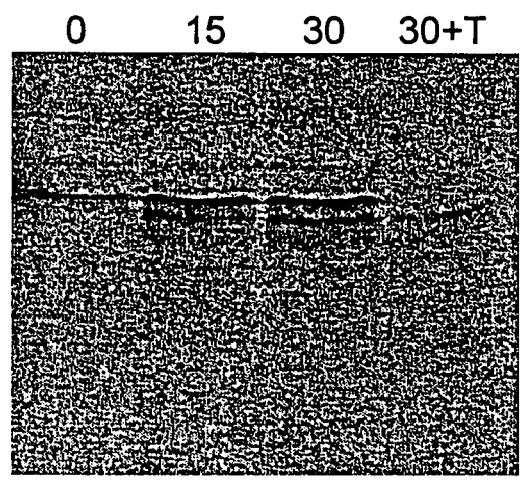
FIG. 3 shows the results of in vitro import of *Arabidopsis thaliana* deformylase (AtDEF1) protein into isolated pea chloroplasts under standard, in vitro import conditions and processing to a mature form once inside the plastid. The 5.5 kD shift from predicted precursor (28.9 kD) to processed (23.4 kD) forms was observed after 15 and 30 minutes after initiation of the assay. Only the processed protein was present after thermolysin treatment of the chloroplasts after 30 minutes of import.

Chloroplast were isolated (Mills and Joy, Planta 148:75-83 (1980)) from 8-10 day old pea seedlings and peptide deformylase was isolated as a bacterially expressed inclusion body (Waegemann and Soll, Methods in Cell Biology 50:255-267). A typical 100 µl import assay contained 330 mM sorbitol, 50 mM Hepes/KOH, pH 7.6, 3 mM MgSO$_4$, 10 mM methionine, 20 mM K-gluconate, 10 mM NaHCO$_3$, 2% BSA, 3 mM ATP, 15-20 mg chlorophyll and 1-2 µl $^{35}$S-methionine labeled peptide deformylase precursor protein (120-600,000 dpm/µl, in 6 M guanidine-HCl). Incubations were performed at room temperature with gentle agitation for 0, 15 or 30 minutes. Following incubation, the chloroplasts were re-isolated through 40% percoll gradients, lysed, resuspended in SDS loading buffer and analyzed by SDS-PAGE. The bacterially-expressed *Arabidopsis thaliana* peptide deformylase protein was imported into isolated pea chloroplasts under standard import conditions and processed to a mature form once inside the plastid. To confirm chloroplast-localization of the mature form of peptide deformylase, chloroplasts were treated with thermolysin (0.1 mg/mg chlorophyll) for 20 minutes on ice following the initial 30 minute incubation. Thermolysin is widely used to confirm precursor import into chloroplasts (See, e.g., Cline et al., Plant Physiol 75:675-678 (1984), Waegemann and Soll, Methods in Cell Biology 18:255-266). The mature form of peptide deformylase imported into isolated chloroplasts was protected from proteolytic (thermolysin) digestion (See FIG. 3.). These import studies prove that *Arabidopsis thaliana* peptide deformylase contains a chloroplast transit peptide and that this cleavable signal sequence is capable and sufficient to direct import of peptide deformylase into isolated chloroplasts.

EXAMPLE 4

*Arabidopsis thaliana* (AtDEF1) Antibody

Strategic BioSolutions (P.O. Box 1319, Ramona, Calif. 92065; 1 800 481 9737) was sent 1 ml of the mature form of AtDEF1 (i.e., ChloroP predicted transit peptide removed; ~23 kDa) in 6M urea, 50 mM Tris, pH 8.2, 5 mM MgCl$_2$, 1 mM EDTA at 4 mg/ml for use in their "Fast Protocol" (50 days) with 2 rabbits. Strategic Biosolutions supplied 1 pre-bleed, 3 bleeds and the final exsanguination.

Figure 4:
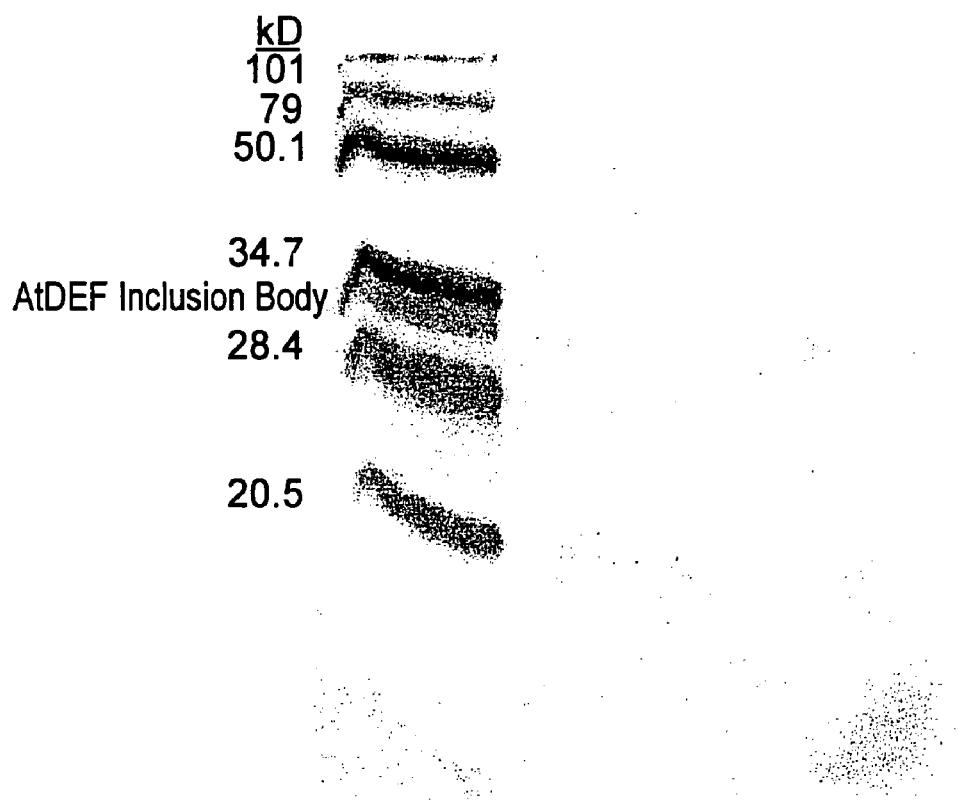

The AtDEF1 antibody (Rabbit 95728) at 1:50,000 detected an expected size protein from ~100 µg *Arabidopsis* total protein extract (See FIG. 4.)

EXAMPLE 5

Assay for in vivo Herbicidal Activity

Pea plants (*Pisum sativum* L. cv. Laxton's Progress No. 9) were sown in 46×62 cm flats of MetroMix 360 and grown for 10-12 days in a greenhouse (minimum night temperature of 30° C.) as described by Wang, P., Royer, M., and Houtz, R. L. Affinity purification of ribulose-1,5-bisphosphate carboxylase/oxygenase large subunit epsilon N-methyltransferase. Protein Expression and Purification 6:528-526 (1995).

Ten-day old pea plants were treated with approximately 100-200 µl actinonin (final concentration. 2.5 mg/ml per plant in 0.1% Tween-20). Control plants were treated with 0.1% Tween-20. As shown in FIG. 5, observable alterations in plant growth, i.e., stunting and yellowing of pea plants, were evident after application of 2.5 mg/ml actinonin. The changes were clearly visible within 48 hours after treatment with actinonin.

EXAMPLE 6

Cloning of Atdef2

A database search revealed that another *Arabidopsis thaliana* genomic sequence (AL163792; ATT15N1 at www.ncbi.nlm.nih.gov; T15N1.150) annotated as "Homology with polypeptide deformylase" is restricted to a small domain with no other sequence homologies in the sequence. Homology was to polypeptide deformylase from Aquifex aeolicus, PIR:C70352.

Both ChloroP v1.1 (130.225.67.199/services/ChloroP1) and TargetP v1.0 (www.cbs.dtu.dk/services/TargetP) predict T15N1.150 to have a 56 amino acid transit peptide to target the protein to the chloroplast.

Primers were designed to amplify PCR products encoding the entire putative protein and the ChloroP-predicted chloroplast-length protein, respectively—(RLH219: 5'-CATATG-GCCGTCTGTAACTGCTTC-3' (SEQ ID NO: 3) and RLH220: 5'-CATATGGCAGAAGTAAAGCGCGTCTC-3' (SEQ ID NO: 4). These primers included an NdeI restriction enzyme site for eventual subcloning into expression vector, pET23. Primers against the 3' end of the genomic sequence encoding the C-terminus of the putative sequence were designed to include the endogenous stop codon and remove the stop codon resulting in a C-terminal 6x. -His tag upon subcloning in the expression vector, respectively (RLH221: 5'-CTCGAGTCAACQTTTGCCAAAACC-3' (SEQ ID NO: 5); RLH222:5'-CTCGAGACGTTTGCCAAAAC-CAAC-3' (SEQ ID NO: 6)). These 3'-end primers included a XhoI restriction enzyme site for eventual subcloning into expression vector, pET23.

RT-PCR

Upon appropriate dilution of the primer stock for a 10 µM working solution, an RT reaction was set up using *Arabidopsis thaliana* cv. Columbia leaf RNA isolated by the TRIzol™ Reagent (Gibco BRL® Life Technologies™) as previously described. The 20 µl reaction contained 2 µl of 10× Gibco BRL® Life Technologies™ PCR Reaction Buffer (200 mM Tris-HCl, pH 8.4, 500 mM KCl), 2 µl of 50 mM Gibco magnesium chloride (final concentration 5 mM), 1 µl of 20 mM dideoxynucleotides (final concentration 1 mM), 11.5 µl of DEPC-treated distilled water, 1 μl of RNA (1.17 μg), 1 μl of 3'-end, 10 μM of primer (RLH221 or RLH222) (final concentration 0.75 μM), and 1 μl of Moloney Murine Leukemia Virus Reverse Transcriptase (10 U/μl) Gibco BRL® Life Technologies™). Fifty microliters of mineral oil was layered on top of the reaction mixture. The reaction was then incubated in a RoboCycler® Gradient 40 Temperature Cycler (Stratagene®, La Jolla, Calif., USA 92037) for 30 minutes at 42° C. and 5 minutes at 99° C.

The PCR product was amplified directly in an RT reaction by the addition of the following: 8 μl of 10× Gibco BRL® Life Technologies™ PCR Buffer (10×: 200 mM Tris-HCl, pH 8.4, 500 mM KCl), 3 μl of 50 mM Gibco BRL® Life Technologies™ magnesium chloride (final concentration 2.5 mM), 67 μl of sterile distilled water, 0.5 μl of Gibco BRL® Life Technologies™ Taq polymerase (5 U/μl), and 1.5 μl of 5'-end primer (10 μM primer RLH219 or 220) (final concentration 0.15 μM). The reaction was then incubated in a RoboCycler® Gradient 40 Temperature Cycler with the following temperature regime: 1 cycle of 3 minutes 94° C.; 35 cycles of 1 minute 94° C., 1 minute 50° C., 1 minute 72° C.; and 1 cycle of 10 minutes 72° C.

Ten microliters of each reaction was loaded into the wells of a 1% agarose gel in TBE buffer (0.09 M Tris-borate, 0.005 M EDTA) (Sambrook, J., Fritsch, E. F., Maniatis, T. Molecular Cloning: A Laboratory Manual, $2^{nd}$ Ed. Cold Spring Harbor Laboratory Press, NY, USA, page B.23 (1989)) containing 0.1 μg/ml ethidium bromide for making the DNA visible under ultraviolet light. Expected product sizes were observed. (FIG. 6.)

To remove excess oligonucleotides, each PCR reaction was purified with QIAquick™ PCR Purification Kit (Cat No. 28104; Qiagen Inc., Valencia, Calif. 91355; used 60 seconds for all steps in the "using a microcentrifuge" protocol (www.qiagen.com/literature/handbooks/qqspin_pcrpure.pdf) and eluted with 50.ul Buffer EB (10 mM Tris-Cl, pH 8.5)).

Ligation to pCR®2.1

Using Invitrogen™'s Original TA Cloning™ Kit (Cat No. K2000-01; Manual available at www.invitrogen.com/manuals.html) and the 3' deoxyadenosine overhang added by the Gibco Taq polymerase, each of the amplicons were cloned separately into the pCR™2.1. A 10 ul reaction mixture was used containing 1 ul of 10× Invitrogen™ Ligation buffer, 1 ul of pCR™2.1 vector (25 ng/ul), 1 ul of QIAquick™ purified-amplicons of reactions RLH219X221, 219X222, 220X221 or 3 ul of QIAquick™ purified-amplicons of reaction RLH220X222, 6 ul and 4 ul, respectively, of sterile water, and 1 ul of T4 DNA Ligase (4.0 Weiss units/ul). The reaction was stirred using a pipette tip. Reaction mixtures were placed immediately at 14° C. in a RoboCycler™ Gradient 40 Temperature Cycler and incubated for 24 hours.

Transformation

Each ligation reaction was transformed separately into rubidium chloride-competent cells as described by Hanahan, D. Techniques for transformation of *E. coli*. In *DNA Cloning. Vol I*, D. M. Glover Ed. IRL Press/Practical Approach Series (1985). Briefly, 100 μl thawed on ice competent DH5α cells were mixed with 2 μl of ligation reaction. The reaction was mixed gently and placed on ice for 30 minutes. The reaction mixture was subsequently plunged into 42° C. water bath for 90 seconds and then immediately placed on ice for 2 minutes. Afterwards, 800 μl of room temperature SOC was added and the reaction was mixed gently and incubated 1 hour at 37° C. with shaking (250 rpm; Series 25 Incubator Shaker, New Brunswick Scientific, Inc., Edison, N.Y., USA). Approximately 650 μl of the reaction mixture was plated onto LB+100 μg/ml ampicillin agar plates with 40 μl (40 mg/ml) X-Gal spread 30 minutes prior to plating. After the majority of the liquid was absorbed by the media, the plates were placed inverted in a 37° C. incubator overnight.

After approximately 12 hours of growth, white colonies were picked with a pipette tip, touched to a new LB+100 μg/ml ampicillin agar plate, and used as innoculum for a 3 ml liquid culture (LB+100 μg/ml ampicillin).

Mini-plasmid Preparation

After approximately 8.5 hours at 37° C. with shaking (as above), a miniprep DNA isolation was performed using a small-scale procedure as described by Sambrook, J., Fritsch, E. F., Maniatis, T. Molecular Cloning: A Laboratory Manual, $2^{nd}$ Ed. Cold Spring Harbor Laboratory Press, NY, USA, pages 1.25-1.28 (1989)), and the final DNA pellet was resuspended in 20 μl of 10 mM Tris, pH 8.0 with 0.1 μg/ml RNase A.

To determine which colonies represented those with Atdef2-containing plasmids, the restriction enzyme sites (EcoRI) immediately flanking either side of the TA-cloning site were cut with the enzyme to release the insert. The 10 μl digest contained 6.7 μl of plasmid DNA, 1 μl of 10× Gibco React 3 (1×: 50 mM Tris-HCl, pH 8.0; 10 mM $MgCl_2$; 100 mM NaCl), 1 μl of 10 mM spermidine-HCl, 1 μl of 10 mg/ml RNase A and 0.3 μl of EcoRI (10 U/μl). The reaction was mixed well and incubated at 37° C. for 1 hour. The entire reaction was loaded into wells of a 1% agarose gel in TBE buffer (0.09 M Tris-borate, 0.005 M EDTA (Sambrook, J., et al. (1989) Molecular Cloning: A Laboratory Manual, $2^{nd}$ Ed. Cold Spring Harbor Laboratory Press, NY, USA, page B.23) containing 0.1 μg/ml ethidium bromide for making the DNA visible under ultraviolet light. Expected product sizes were observed. (FIG. 6)

Reactions which released a fragment of nearly identical size to the initial PCR reaction (RLH219X221 or 222=~830 bp; RLH220X221 or 222=~660 bp) were used for subcloning experiments. The reactions were designated as follows: #1-2: RLH219X221, #2-2: RLH219X222, #3-1: RLH220X221, and #4-D: RLH220X222.

EXAMPLE 7

Subcloning of Atdef2 and Expression of AtDEF2

To prepare the Atdef2 insert for subcloning into pET23, the restriction enzyme sites (NdeI and XhoI) engineered into the oligonucleotides used to RT-PCR the RNA were used to release the insert. Four separate 50 μl digests were set up to contain 32 μl of plasmid DNA, 5 μl of 10× Gibco React 2 (1×: 50 mM Tris-HCl, pH 8.0; 10 mM $MgCl_2$; 50 mM NaCl), 5 μl of 10 mM spermidine-HCl, 5 μl of RNase A (10 mg/ml), 1.5 μl of NdeI (5 U/μl) and 1.5 μl of XhoI (10 U/μl). The reaction was mixed well and incubated at 37° C. for 4 hours. A further aliquot of 1× Enzyme Mix (as below) was added and mixed to ensure complete digestion. The 1× Enzyme Mix contained 3 μl of 10× Gibco React 2 (1×: 50 mM Tris-HCl, pH 8.0; 10 mM $MgCl_2$; 50 mM NaCl), 3 μl of 10 mM spermidine-HCl, 3 μl of 10 mg/ml RNase A, 19.2 μl of sterile water, 0.9 μl of NdeI (5 U/μl), and 0.9 μl of XhoI (10 U/μl). The reaction was mixed well and incubated at 37° C. for 17 hours. Half of each reaction was loaded into large wells of a 1.5% low melting point agarose (Gibco Life Technologies Cat No. 15517-022) gel in TA buffer (0.04 M Tris-acetate), (Sambrook, J., et al. Molecular Cloning: A Laboratory Manual, $2^{nd}$ Ed. Cold Spring Harbor Laboratory Press, NY, USA, page B.23 (1989)) containing 0.1 μg/ml ethidium bromide for making the DNA visible under ultraviolet light. The Atdef2 insert with 5'-NdeI/3'-XhoI ends were cut from the gel.

Restriction endonuclease digested pET23a (NdeI/XhoI) vector was prepared as follows: Approximately 2 µg of Qiagen prepped plasmid DNA was digested with 5 units NdeI (5 U/µl) and 5 units XhoI (10 U/µl) for 2 hours at 37° C. Following digestion, the pET23a plasmid was purified on a 1% agarose gel using the Qiaquick gel purification kit (Qiagen). Four microliters were used in the ligation reactions.

The vector pET23b (Novagen, www.novagen.com/, 601 Science Drive, Madison, Wis., 53711) was digested as follows. Approximately 7.9 ul of pET23b (0.38 ng/ul) was added to a reaction mixture containing 5 ul of 10× Gibco React 2 (1×: 50 mM Tris-HCl, pH 8.0; 10 mM $MgCl_2$; 50 mM NaCl), 5 ul of 10 mM spermidine-HCl, 5 ul of 10 mg/ml RNase A, 29.1 ul of sterile water, 1.5 ul of NdeI (5 U/ul), and 1.5 ul of XhoI (10 U/ul). The 50 ul reaction was mixed well and incubated at 37° C. for 12 hours.

A further aliquot of 1× Enzyme Mix (as below) was added and mixed to ensure complete digestion. The 30 µl reaction contained 3 µl of 10× Gibco React 2 (1×: 50 mM Tris-HCl, pH 8.0; 10 mM $MgCl_2$; 50 mM NaCl), 3 µl of 10 mM spermidine-HCl, 3 µl of 10 mg/ml RNase A, 19.2 µl of sterile water, 0.9 µl of NdeI (5 U/µl), and 0.9 µl of XhoI (10 U/µl). The reaction was mixed well and incubated at 37° C. for 9 hours. The reaction was then loaded into a large well of a 1.5% low melting point agarose (Gibco Life Technologies Cat No. 15517-022) gel in TA buffer and the linearized vector band cut from the gel.

Ligation of Atdef2 to pET23b

The Atdef2 insert was ligated to the linearized vector as follows. A 10 ul reaction was set up containing 1 ul of 10× New England Biolabs™ Inc. (NEB) Ligase Buffer (1×: 50 mM Tris-HCl, pH 7.5, 10 mM $MgCl_2$, 10 mM dithiothreitol, 1 mM of ATP, 25 ug/ml of bovine serum albumin) (NEB at www.neb.com/, Beverly, Mass. 01915-5599), 1 ul of pET23a for reaction mixtures #1-2 and #3-1, 7 ul of 70° C.-heated, agarose containing Atdef2 prepared by cutting with NdeI and XhoI, and 1 ul of NEB T4 DNA Ligase (400,000 units/ml; NEB Cat No. 202S). The reaction was mixed well and incubated at 15° C. for approximately 15.5 hours.

For samples #2-2 and #4-D, the 10 µl ligation reaction mixture contained 1 µl of 10× NEB Ligase Buffer, 3 µl of 70° C.-heated, agarose containing pET23b linearized with NdeI and XhoI, 5 µl of 70° C.-heated, agarose containing Atdef2 prepared by cutting with NdeI and XhoI, and 1 µl NEB T4 DNA Ligase (400,000 units/ml; NEB Cat No. 202S). The reaction was mixed well and incubated at 15° C. for approximately 15.5 hours.

Transformation

For the transformations, 3 µl of 70° C.-heated, agarose containing ligation was mixed with 100 µl $CaCl_2$-competent DH5α cells as described by Sambrook, J., et al. Molecular Cloning: A Laboratory Manual, $2^{nd}$ Ed. Cold Spring Harbor Laboratory Press, NY, USA, page 1.82 to 1.84 . (1989))

The reactions were mixed well but gently and incubated on ice for 30 minutes, plunged into 42° C. water bath for 45 seconds, and then immediately into ice for 2 minutes. Subsequently, 250 µl of room temperature SOC was added, and the reaction was mixed gently and incubated 1 hour at 37° C. with shaking (250 rpm; Series 25 Incubator Shaker, New Brunswick Scientific, Inc., Edison, N.Y., USA). The entire transformation mixture was plated onto LB+100 µg/ml ampicillin agar plates. After the majority of the liquid was absorbed by the media, the plates were placed inverted in a 37° C. incubator overnight.

After approximately 12 hours of growth, colonies were picked with a pipette tip, touched to a new LB+100 µg/ml ampicillin agar plate, and used as innoculum for a 5 ml liquid LB+100 µg/ml ampicillin. After approximately 16 hours at 37° C. with shaking, a miniprep DNA isolation was conducted using a small-scale procedure (Sambrook, J., et al. Molecular Cloning: A Laboratory Manual, $2^{nd}$ Ed. Cold Spring Harbor Laboratory Press, NY, USA, pages 1.25-1.28 (1989)), resuspending the final DNA pellet in 30 µl 10 mM Tris, pH 8.0 with 0.1 µg/ml RNase A.

To determine which colonies represented those with Atdef2-containing plasmids, the restriction enzyme sites (NdeI and XhoI) immediately flanking either side of the TA-cloning site were cut with the enzymes to release the insert. The 10 µl digest was set up to contain 5 µl of plasmid DNA, 1 µl of 10× Gibco React 2 (1×: 50 mM Tris-HCl, pH 8.0; 10 mM $MgCl_2$; 50 mM NaCl), 1 µl of 10 mM spermidine-HCl, 1 µl of RNase A (10 mg/ml), 1.4 µl of sterile water, 0.3 µl of NdeI (5 U/µl) and 0.3 µl of XhoI (10 U/µl). The reaction was mixed well and incubated at 37° C. for 1 hour.

The entire reaction was loaded into wells of a 1% agarose gel in TBE buffer (0.09 M Tris-borate, 0.005 M EDTA) as described by Sambrook, J., et al. (1989) Molecular Cloning: A Laboratory Manual, 2nd Ed Cold Spring Harbor Laboratory Press, NY, USA, page B.23) containing 0.1 ug/ml ethidium bromide for making the DNA visible under ultraviolet light. Those reactions which released a fragment of identical size as the Atdef2 insert used in the ligation reaction were used for transforming the expression cell line, BL21(DE3)pLysS (Novagen, www.novagen.com/html/catfram.html Cat No. 69451-3).

Approximately 1 to 1.5 µl of plasmid DNA from the above miniprep DNA preparation were mixed with 20 µl BL21 (DE3)pLysS competent cells (Novagen, Cat No. 69451-3). The reaction mixture was incubated on ice for 5 minutes, mixed well, but gently, and plunged into 42° C. water bath for 30 seconds and then immediately into ice for 2 minutes. Subsequently, 80 µl of room temperature SOC were added and the reaction was mixed gently and incubated 1 hour at 37° C. with shaking (250 rpm; Series 25 Incubator Shaker, New Brunswick Scientific, Inc., Edison, N.Y., USA). The entire transformation mixture was plated onto LB+100 µg/ml ampicillin+34 µg/ml chloramphenicol agar plates. After the majority of the liquid was absorbed by the media, the plates were placed inverted in a 37° C. incubator overnight.

Induction of AtDEF2

Given that the predicted transit peptide would be cleaved prior to the protein becoming active within the chloroplast, only #3-1 and #4-D were used in trial expressions. Furthermore, due to the ease of a purification with the inframe 6×His-tag, #4-D was used exclusively in temperature studies to alter solubility of expressed proteins.

The expected sizes of the protein with and without the transit peptide were 30.6 and 24.6 kDa, respectively. However, the *E. coli* enzyme, predicted to be 19.197 kDa; has varying mobility from 19-23 kDa and thus, AtDEF2 may also run anomalously (Rajagopalan P. T. R., Datta A., and Pei, D. Purification, characterization, and inhibition of peptide deformylase from *Escherichia coli*. Biochemistry 36:13910-13918 (1997)).

A single colony of #4-D (in BL21(DE3)pLysS cells) was used to innoculate 3 ml liquid LB+100 µg/ml ampicillin+34 µg/ml chloramphenicol. After approximately 3 hours of growth and with an absorbance (600 nm) of approximately 0.4, one ml of the culture was subcultured into 34 ml of the same selective media. After a further 3 hours of growth and a similar absorbance, the culture was subdivided into 5 ml aliquots to allow induction at room temperature or 30° C. combined with 0, 0.4 or 1.0 mM final IPTG (isopropyl b-D-thiogalactopyranoside) concentrations and 2 hours and overnight (approximately 23.5 hours) time points.

At respective time points, 2.5 ml of the culture was placed in an ice-chilled microcentrifuge tube for 5 minutes before centrifuging (14,000 rpm, 5 minutes, 4° C., model MR18.12 Jouan refrigerated centrifuge, Winchester, Va. 22602, USA) to collect the cells. The liquid media was aspirated away and, prior to freezing at −70° C., the cells resuspended 125 times more concentrated than the original culture in standard buffer (50 mM Tris, pH 8.2, 5 mM $MgCl_2$, 1 mM EDTA)+100 µM $NiSO_4$. After 3 repeated freeze/thaw cycles, the lysed cells were sonicated 2×10 second pulses with a Branson Sonifier 250 (Branson Sonic Power Company, Danbury, Conn.) at half power, keeping the cells on ice. Subsequently, the lysed, sonicated cells were centrifuged (14,000 rpm, 5 minutes, 4° C., model MR18.12 Jouan refrigerated centrifuge, Winchester, Va. 22602, USA). The supernatant represents the soluble proteins. The pellet was suspended in a similar volume of standard buffer+100 µM $NiSO_4$ in which the cells were originally suspended and this represents the insoluble proteins. To 7.5 µl soluble and insoluble proteins, an equal volume of 2× sample buffer (0.125M Tris-HCl, pH 6.8, 4% SDS, 10% 2-mercaptoethanol, 20% sucrose, 0.004% bromophenol blue) was added before boiling for 3 minutes (Hames, B. D., and Rickwood, D. Gel electrophoresis of proteins: A practical approach. IRL Press, Washington, D.C., USA page 37 (1981)). The samples were collected by a brief centrifugation prior to loading into respective wells of a 10 well, 15% polyacrylamide gel containing SDS (SDS-PAGE) (Hames, B. D., and Rickwood, D. Gel electrophoresis of proteins: A practical approach. IRL Press, Washington, D.C., USA (1981)). Given that significant amounts of protein were seen in the soluble portion, assays were conducted with the remaining soluble protein. Due to observed activity, a further culture was induced for His-purification of the soluble protein to ensure that activity was due only to the plant deformylase and not to any endogenous bacterial deformylase.

His-purification of AtDEF2

A single colony of #4D in BL21(DE3)pLysS cells was used for inoculating 3 ml LB+100 mg/ml ampicillin +34 mg/ml chloramphenicol and grown overnight at 37° C. A 1 ml aliquot was used to sub-innoculate 100 ml, selective media and grown at 37° C. to an absorbance (600 nm) of 0.409 in 2.5 hours. IPTG was added to a final concentration of 0.4 mM and the culture shaken at approximately 23° C. for approximately 21.5 hours. After 5 minutes on ice, the cells were harvested (centrifuged 5 minutes, 40° C., 5000×g). To the pellet, 4 ml binding buffer (5 mM imidazole, 0.5M NaCl, 20 mM Tris-HCl, pH 7.9; Novagen, Inc., pET System Manual, 6$^{th}$ Ed.)+ 100 uM $NiSO_4$ (for preservation of enzyme activity) was added and the cells resuspended. This resuspension was sonicated 5×10 seconds pulses with a Branson Sonifier 250 (Branson Sonic Power Company, Danbury, Conn.) at half power, keeping the cells on ice during the whole time and waiting a minute between pulses. After centrifuging (39,200× g, 4° C., 20 minutes), the supernatant was decanted into approximately 2.5 ml settled volume of charged His.cndot. .Bind™ resin (Novagen, Cat. No. 69670; "Resin preparation" section of TB054, page 9: His.cndot.Bind™ Kits (65K pdf) found in TechLit of Novagen's website www.novagen.com site). A batchwise fashion purification was followed by centrifuging the resin at 500×g after a 30 minute binding step on ice. Similar amounts of washing steps were performed as suggested for "Column Chromatography" ("Resin preparation" section of TB054, page 9: His.cndot.Bind™ Kits found in TechLit of Novagen's website www.novagen.com/site; buffer composition page 3). AtDEF2 was eluted by incubating with 1 ml elution buffer (IM imidazole, 0.5M NaCl, 20 mM Tris-HCl, pH 7.9) for 30 minutes on ice with gentle rocking. The elution was separated from the resin by centrifuging at 500×g and the eluted protein tested for peptide deformylase activity.

As seen in FIG. 7, the protein eluted from the His•Bind® resin is larger than the predicted 24.6 kDa. Thus, AtDEF2 appears to have migrated ~4 kDa higher than predicted but, as mentioned above, the *E. coli* enzyme, predicted to be 19.197 kDa, migrates as much as 4 kDa greater than its predicted size (Rajagopalan P. T. R., Datta A., and Pei; D. Purification, characterization, and inhibition of peptide deformylase from *Escherichia coli*. Biochemistry 36:13910-13918 (1997)).

EXAMPLE 8

Peptide Deformylase Activity and Inhibition

Experiments were designed to detect deformylase activity from recombinant AtDEF2 using the assay as described by Wei and Pei, Analytical Biochemistry 250:29-34 (1997).

Continuous spectrophotometric assays of peptide deformylase activity were carried out at a temperature of 20° C. Assays were performed in polystyrene or quartz cuvettes containing 50 mM Tris-HCl, pH 8.2, 1 mM ethylene diamine bis(β-aminoethyl ether-N,N'-tetraacetic acid (EDTA), 5 mM $MgCl_2$, 200 µM $NiSO_4$ 0-200 µM peptide substrate and 1.0 units of *Aeromonas proteolytica* aminopeptidase. The reactions were initiated by the addition of 10-100 µl (0.1-100 µg) of deformylase enzyme. that had been diluted in 50 mM Hepes, pH 7.0, 100 µg/ml bovine serum albumin. The reactions were monitored continuously at 405 nm in a Shimadzu UV-201 PC scanning spectrophotometer, and the initial rates were calculated from the early part of the reaction progression curves (<60 s).

Spectrophotometric detection and quantitation was performed of p-nitroaniline released from formyl-Met-Leu-p-nitroanilide substrate (BACHEM Cat. No. L2030; King of Prussia, Pa. 19406 USA) following sequential action of AtDEF2 and *Aeromonas proteolytica* aminopeptidase (Sigma Cat. No. A8200; St. Louis, Mo., 63118 USA).

As indicated by the data in FIG. 8, including actinonin, a naturally occurring antibacterial agent and potent deformylase inhibitor (Chen et al., Biochemistry, (2000) 39(6):1256-1263), significantly inhibited the activity of AtDEF2 within 60 seconds. Moreover, by preincubating the actinonin with AtDEF2 first (43.5 µg AtDEF2 preincubated 3 minutes with 3.2 µM actinonin) and then initiating the assay with substrate, nearly complete inhibition of deformylase activity was observed.

We claim:

1. A method of preparing an herbicide-resistant plant, comprising: a) transforming recipient plant cells with a nucleic acid molecule encoding a plant peptide deformylase having peptide deformylase activity; b) selecting a recipient plant cell comprising the nucleic acid molecule, c) contacting the selected recipient plant cell of (b) with an herbicide that inhibits plant peptide deformylase activity; d) selecting a recipient plant cell of (c) that is resistant to the herbicide; and e) regenerating a plant from the selected recipient plant cell, wherein the plant comprises enhanced herbicide resistance relative to a corresponding non-transformed plant and wherein the plant peptide deformylase comprises the amino acid sequence of SEQ ID NO: 8.

2. The method according to claim 1 wherein the herbicide comprises actinonin.

3. A method of controlling weeds comprising the step of planting an herbicide resistant plant prepared according to the method of claim 1 and treating the plants, and the area in proximity to said plants, with a plant peptide deformylase-inhibiting herbicide, wherein growth of weeds is controlled.

4. The method according to claim 3 wherein the herbicide comprises actinonin.

5. A method of selectively growing herbicide-resistant plants, the method comprising the steps of: a) growing plants comprising elevated levels of plant peptide deformylase relative to a corresponding wild type plant; and b) contacting the plants with an amount of an herbicide comprising an inhibitor of plant peptide deformylase sufficient to prevent growth of a corresponding plant which does not over-express plant peptide deformylase wherein the plant peptide deformylase is encoded by a transgene and wherein the plant peptide deformylase comprises the amino acid sequence of SEQ ID NO: 8.

6. The method according to claim 5 wherein the herbicide comprises actinonin.

* * * * *

SEQUENCE LISTING

<160> NUMBER OF SEQ ID NOS: 10

<210> SEQ ID NO 1
<211> LENGTH: 21
<212> TYPE: DNA
<213> ORGANISM: Arabidopsis thaliana
<220> FEATURE:
<221> NAME/KEY: misc_feature
<222> LOCATION: (1)..(21)
<223> OTHER INFORMATION: Primer RLH 146

<400> SEQUENCE: 1
ttgtcgacaa aagccggttg g                                         21

<210> SEQ ID NO 2
<211> LENGTH: 20
<212> TYPE: DNA
<213> ORGANISM: Arabidopsis thaliana
<220> FEATURE:
<221> NAME/KEY: misc_feature
<222> LOCATION: (1)..(20)
<223> OTHER INFORMATION: Primer RLH 147

<400> SEQUENCE: 2
tcattgaggt ccgagcttag                                           20

<210> SEQ ID NO 3
<211> LENGTH: 24
<212> TYPE: DNA
<213> ORGANISM: Arabidopsis thaliana
<220> FEATURE:
<221> NAME/KEY: misc_feature
<222> LOCATION: (1)..(24)
<223> OTHER INFORMATION: Primer RLH 219

<400> SEQUENCE: 3
catatggccg tctgtaactg cttc                                      24

<210> SEQ ID NO 4
<211> LENGTH: 26
<212> TYPE: DNA
<213> ORGANISM: Arabidopsis thaliana
<220> FEATURE:
<221> NAME/KEY: misc_feature
<222> LOCATION: (1)..(26)
<223> OTHER INFORMATION: Primer RLH 220

<400> SEQUENCE: 4
catatggcag aagtaaagcg cgtctc                                    26

<210> SEQ ID NO 5
<211> LENGTH: 24
<212> TYPE: DNA
<213> ORGANISM: Arabidopsis thaliana
<220> FEATURE:
<221> NAME/KEY: misc_feature
<222> LOCATION: (1)..(24)
<223> OTHER INFORMATION: Primer RLH 221

<400> SEQUENCE: 5
ctcgagtcaa cgtttgccaa aacc                                      24

<210> SEQ ID NO 6
<211> LENGTH: 24
<212> TYPE: DNA
<213> ORGANISM: Arabidopsis thaliana

```
<220> FEATURE:
<221> NAME/KEY: misc_feature
<222> LOCATION: (1)..(24)
<223> OTHER INFORMATION: Primer RLH 222

<400> SEQUENCE: 6
ctcgagacgt tgccaaaac caac                                                  24

<210> SEQ ID NO 7
<211> LENGTH: 169
<212> TYPE: PRT
<213> ORGANISM: Escherichia coli

<400> SEQUENCE: 7
```

Met Ser Val Leu Gln Val Leu His Ile Pro Asp Glu Arg Leu Arg Lys
1               5                   10                  15

Val Ala Lys Pro Val Glu Val Asn Ala Glu Ile Gln Arg Ile Val
            20                  25                  30

Asp Asp Met Phe Glu Thr Met Tyr Ala Glu Gly Ile Gly Leu Ala
            35                  40                  45

Ala Thr Gln Val Asp Ile His Gln Arg Ile Ile Val Ile Asp Val Ser
        50                  55                  60

Glu Asn Arg Asp Glu Arg Leu Val Leu Ile Asn Pro Glu Leu Leu Glu
65                  70                  75                  80

Lys Ser Gly Glu Thr Gly Ile Glu Glu Gly Cys Leu Ser Ile Pro Glu
                85                  90                  95

Gln Arg Ala Leu Val Pro Arg Ala Glu Lys Val Lys Ile Arg Ala Leu
            100                 105                 110

Asp Arg Asp Gly Lys Pro Phe Glu Leu Glu Ala Asp Gly Leu Leu Ala
        115                 120                 125

Ile Cys Ile Gln His Glu Met Asp His Leu Val Gly Lys Leu Met Phe
130                 135                 140

Asp Tyr Leu Ser Pro Leu Lys Gln Gln Arg Ile Arg Gln Lys Val Glu
145                 150                 155                 160

Lys Leu Asp Arg Leu Lys Ala Arg Ala
                165

```
<210> SEQ ID NO 8
<211> LENGTH: 259
<212> TYPE: PRT
<213> ORGANISM: Arabidopsis

<400> SEQUENCE: 8
```

Met Glu Thr Leu Phe Arg Val Ser Leu Arg Leu Leu Pro Val Ser Ala
1               5                   10                  15

Ala Val Thr Cys Arg Ser Ile Arg Phe Pro Val Ser Arg Pro Gly Ser
            20                  25                  30

Ser His Leu Leu Asn Arg Lys Leu Tyr Asn Leu Pro Thr Ser Ser Ser
            35                  40                  45

Ser Ser Leu Ser Thr Lys Ala Gly Trp Leu Gly Leu Gly Glu Lys
        50                  55                  60

Lys Lys Lys Val Asp Leu Pro Glu Ile Val Ala Ser Gly Asp Pro Val
65                  70                  75                  80

Leu His Glu Lys Ala Arg Glu Val Asp Pro Gly Glu Ile Gly Ser Glu
                85                  90                  95

Arg Ile Gln Lys Ile Ile Asp Asp Met Ile Lys Val Met Arg Leu Ala
            100                 105                 110

```
Pro Gly Val Gly Leu Ala Ala Pro Gln Ile Gly Val Pro Leu Arg Ile
        115                 120                 125

Ile Val Leu Glu Asp Thr Lys Glu Tyr Ile Ser Tyr Ala Pro Lys Glu
    130                 135                 140

Glu Ile Leu Ala Gln Glu Arg Arg His Phe Asp Leu Met Val Met Val
145                 150                 155                 160

Asn Pro Val Leu Lys Glu Arg Ser Asn Lys Lys Ala Leu Phe Phe Glu
                165                 170                 175

Gly Cys Leu Ser Val Asp Gly Phe Arg Ala Ala Val Glu Arg Tyr Leu
            180                 185                 190

Glu Val Val Thr Gly Tyr Asp Arg Gln Gly Lys Arg Ile Glu Val
        195                 200                 205

Asn Ala Ser Gly Trp Gln Ala Arg Ile Leu Gln His Glu Cys Asp His
    210                 215                 220

Leu Asp Gly Asn Leu Tyr Val Asp Lys Met Val Pro Arg Thr Phe Arg
225                 230                 235                 240

Thr Val Asp Asn Leu Asp Leu Pro Leu Ala Glu Gly Cys Pro Lys Leu
                245                 250                 255

Gly Pro Gln

<210> SEQ ID NO 9
<211> LENGTH: 209
<212> TYPE: PRT
<213> ORGANISM: Arabidopsis

<400> SEQUENCE: 9

Leu Ser Thr Lys Ala Gly Trp Leu Leu Gly Leu Gly Glu Lys Lys Lys
1               5                   10                  15

Lys Val Asp Leu Pro Glu Ile Val Ala Ser Gly Asp Pro Val Leu His
                20                  25                  30

Glu Lys Ala Arg Glu Val Asp Pro Gly Glu Ile Gly Ser Glu Arg Ile
            35                  40                  45

Gln Lys Ile Ile Asp Asp Met Ile Lys Val Met Arg Leu Ala Pro Gly
        50                  55                  60

Val Gly Leu Ala Ala Pro Gln Ile Gly Val Pro Leu Arg Ile Ile Val
65                  70                  75                  80

Leu Glu Asp Thr Lys Glu Tyr Ile Ser Tyr Ala Pro Lys Glu Glu Ile
                85                  90                  95

Leu Ala Gln Glu Arg Arg His Phe Asp Leu Met Val Met Val Asn Pro
            100                 105                 110

Val Leu Lys Glu Arg Ser Asn Lys Lys Ala Leu Phe Phe Glu Gly Cys
        115                 120                 125

Leu Ser Val Asp Gly Phe Arg Ala Ala Val Glu Arg Tyr Leu Glu Val
    130                 135                 140

Val Val Thr Gly Tyr Asp Arg Gln Gly Lys Arg Ile Glu Val Asn Ala
145                 150                 155                 160

Ser Gly Trp Gln Ala Arg Ile Leu Gln His Glu Cys Asp His Leu Asp
                165                 170                 175

Gly Asn Leu Tyr Val Asp Lys Met Val Pro Arg Thr Phe Arg Thr Val
            180                 185                 190

Asp Asn Leu Asp Leu Pro Leu Ala Glu Gly Cys Pro Lys Leu Gly Pro
        195                 200                 205

Gln
```

```
-continued

<210> SEQ ID NO 10
<211> LENGTH: 186
<212> TYPE: PRT
<213> ORGANISM: Chlamydia

<400> SEQUENCE: 10

Met Ile Arg Arg Leu Glu Tyr Tyr Gly Ser Pro Ile Leu Arg Lys Lys
1               5                   10                  15

Ser Ser Pro Ile Ala Glu Ile Thr Asp Glu Ile Arg Asn Leu Val Ser
            20                  25                  30

Asp Met Cys Asp Thr Met Glu Ala His Arg Gly Val Gly Leu Ala Ala
        35                  40                  45

Pro Gln Val Gly Lys Asn Val Ser Leu Phe Val Met Cys Val Asp Arg
    50                  55                  60

Glu Thr Glu Asp Gly Glu Leu Ile Phe Ser Glu Ser Pro Arg Val Phe
65                  70                  75                  80

Ile Asn Pro Val Leu Ser Asp Pro Ser Glu Thr Pro Ile Ile Gly Lys
                85                  90                  95

Glu Gly Cys Leu Ser Ile Pro Gly Leu Arg Gly Glu Val Phe Arg Pro
            100                 105                 110

Gln Lys Ile Thr Val Thr Ala Met Asp Leu Asn Gly Lys Ile Phe Thr
        115                 120                 125

Glu His Leu Glu Gly Phe Thr Ala Arg Ile Ile Met His Glu Thr Asp
    130                 135                 140

His Leu Asn Gly Val Leu Tyr Ile Asp Leu Met Glu Glu Pro Lys Asp
145                 150                 155                 160

Pro Lys Lys Phe Lys Ala Ser Leu Glu Lys Ile Lys Arg Arg Tyr Asn
                165                 170                 175

Thr His Leu Ser Lys Glu Glu Leu Val Ser
            180                 185
```